US008288169B2

(12) United States Patent　　(10) Patent No.: US 8,288,169 B2
Utermohlen et al.　　(45) Date of Patent: *Oct. 16, 2012

(54) SURFACE MEDIATED SELF-ASSEMBLY OF NANOPARTICLES

(75) Inventors: Joseph G. Utermohlen, Tucson, AZ (US); Michael E. Hogan, Tucson, AZ (US); Paul E. Diggins, Tucson, AZ (US)

(73) Assignee: Argylla Technologies, Tucson, AZ (US)

( * ) Notice: Subject to any disclaimer, the term of this patent is extended or adjusted under 35 U.S.C. 154(b) by 844 days.

This patent is subject to a terminal disclaimer.

(21) Appl. No.: 12/054,325

(22) Filed: Mar. 24, 2008

(65) Prior Publication Data

US 2009/0182120 A1　Jul. 16, 2009

Related U.S. Application Data

(63) Continuation-in-part of application No. 11/338,124, filed on Jan. 23, 2006.

(60) Provisional application No. 60/896,479, filed on Mar. 22, 2007, provisional application No. 60/646,155, filed on Jan. 21, 2005, provisional application No. 60/701,630, filed on Jul. 22, 2005.

(51) Int. Cl.
*G01N 1/18* (2006.01)
*C12Q 1/68* (2006.01)
(52) U.S. Cl. .............................. 436/177; 435/6; 514/951
(58) Field of Classification Search ........................ None
See application file for complete search history.

(56) References Cited

U.S. PATENT DOCUMENTS

| | | | |
|---|---|---|---|
| 4,102,977 A | 7/1978 | Sugahara et al. | |
| 4,540,486 A | 9/1985 | Ramsden | |
| 4,554,088 A | 11/1985 | Whitehead et al. | |
| 4,672,040 A | 6/1987 | Josephson | |
| 4,677,027 A | 6/1987 | Porath et al. | |
| 4,677,067 A | 6/1987 | Schwartz et al. | |
| 4,695,392 A | 9/1987 | Whitehead et al. | |
| 4,695,393 A | 9/1987 | Whitehead et al. | |
| 4,696,980 A | 9/1987 | Porath | |
| 4,698,302 A | 10/1987 | Whitehead et al. | |
| 4,897,467 A | 1/1990 | Porath | |
| 4,921,805 A | 5/1990 | Gebeyehu et al. | |
| 5,091,206 A | 2/1992 | Wang et al. | |
| 5,141,966 A | 8/1992 | Porath | |
| 5,185,313 A | 2/1993 | Porath | |
| 5,523,231 A | 6/1996 | Reeve | |
| 5,582,988 A | 12/1996 | Backus et al. | |
| 5,622,822 A | 4/1997 | Ekeze et al. | |
| 5,652,141 A | 7/1997 | Henco et al. | |
| 5,681,946 A | 10/1997 | Reeve | |
| 5,705,628 A | 1/1998 | Hawkins | |
| 5,898,071 A | 4/1999 | Hawkins | |
| 5,942,463 A | 8/1999 | Oscarsson et al. | |
| 6,395,029 B1 | 5/2002 | Levy | |
| 6,552,114 B2 | 4/2003 | Turner et al. | |

(Continued)

OTHER PUBLICATIONS http://www.geocities.com/gemowery/CircularPeriodicTableofElements.html, retrieved from the internet Dec. 16, 2005.*

(Continued)

*Primary Examiner* — Robert T. Crow
(74) *Attorney, Agent, or Firm* — Donna E. Becker

(57) ABSTRACT

Materials and methods for surface mediated self-assembly of nanoparticles for the isolation of biomolecules is provided.

16 Claims, 8 Drawing Sheets

DNA Adsorption to 40nm Nanoparticles Occurs Rapidly Due to Large Surface Area Displayed by NanoParticles and with a Small Separation Between Particles

U.S. PATENT DOCUMENTS

| | | | |
|---|---|---|---|
| 6,585,822 B2* | 7/2003 | Berube et al. | 428/32.34 |
| 6,596,699 B2 | 7/2003 | Zamora et al. | |
| 6,602,718 B1 | 8/2003 | Augello et al. | |
| 6,623,982 B1* | 9/2003 | Liberti et al. | 436/526 |
| 6,718,742 B1 | 4/2004 | Baker | |
| 2002/0034827 A1* | 3/2002 | Singh et al. | 436/177 |
| 2002/0103095 A1* | 8/2002 | Becker et al. | 510/305 |
| 2002/0160098 A1 | 10/2002 | Zamora et al. | |
| 2003/0059955 A1* | 3/2003 | Bamdad | 436/524 |
| 2003/0077839 A1* | 4/2003 | Takei | 436/177 |
| 2003/0124194 A1* | 7/2003 | Gaw et al. | 424/491 |

OTHER PUBLICATIONS

Cotton et al, Advanced Inorganic Chemistry, 5th ed., Wiley-Interscience, New York, 1988, inside back cover.*

The defintiion of "matrix" provided by by the online dictionary at dictionary.cambridge.org [retrieved on Nov. 29, 2010]. Retrieved from the Internet: <URL: dictionary.cambridge.org/dictionary/british/matrix>.*

Alderton, et al., "Isolation of lysozyme from egg white," J. Biol. Chem., 157:43-58 (1945).

Davies, et al., "Isolation of Plasmid DNA Using Magnetite as a Solid-Phase Adsorbent," Analytical Biochemistry, 262: 92-94 (1998).

Friedman and Yellen, "Magnetic separation, manipulation and assembly of solid phase in fluids," Current Opinion in Colloid & Interface Science 10: 158-166 (2005).

Salata, "Applications of nanoparticles in biology and medicine," Journal of Nanobiotechnology, 2:3 (2004).

Yoza, et al., "DNA extraction using modified bacterial magnetic particles in the presence of amino silane compound," Journal of Biotechnology 94: 217-224 (2002).

Berensmeier, Magnetic particles for the separation and purification of nucleic acids, Appl Microbiol Biotechnol, 73: 495-504 (2006).

Davies, et al., Isolation of Plasmid DNA Using Magnetite as a Solid-Phase Adsorbent, Analytical Biochemistry, 262: 92-94 (1998).

GenomeWeb.com, GE Healthcare, Beckman Coulter Settle Nucleic Acid Sample Prep Lawsuit, Jul. 21, 2011.

Leslie-Pelecky, et al., Magnetic Properties of Nanostructured Materials, Chem Mater, 8: 1770-1783 (1996).

Molday, et al., Application of magnetic microspheres in labelling and separation of cells, Nature, 268: 437-438 (1977).

Novagen, MagPrep Bacterial Genomic DNA Kit (product information).

Novagen, MagPrep Bacterial Genomic DNA Kit (email from Jeffrey C. Hsu, Oct. 14, 2011).

Prodelalova, et al., Isolation of genomic DNA using magnetic cobalt ferrite and silica particles, Journal of Chromatography A, 1056: 43-48 (2004).

Saiyed, et al., Application of magnetic particles (Fe3O4) for isolation of genomic DNA from mammalian cells, Analytical Biochemistry, 356: 306-308 (2006).

Taylor et al., Application of magnetite and silica-magnetite composites to the isolation of genomic DNA, Journal of Chromatography A, 890: 159-166 (2000).

Yoza et al., DNA extraction using modified bacterial magnetic particles in the presence of amino silane compound, Journal of Biotechnology, 94: 217-224 (2002).

Oct. 21, 2011 Joseph G. Utermohlen correspondence.
Oct. 21, 2011 Joseph G. Utermohlen email.
Oct. 31, 2011 Joseph G. Utermohlen email.
Nov. 7, 2011 Joseph G. Utermohlen email.
Nov. 8, 2011 Joseph G. Utermohlen email.
Nov. 9, 2011 Joseph G. Utermohlen email.

* cited by examiner

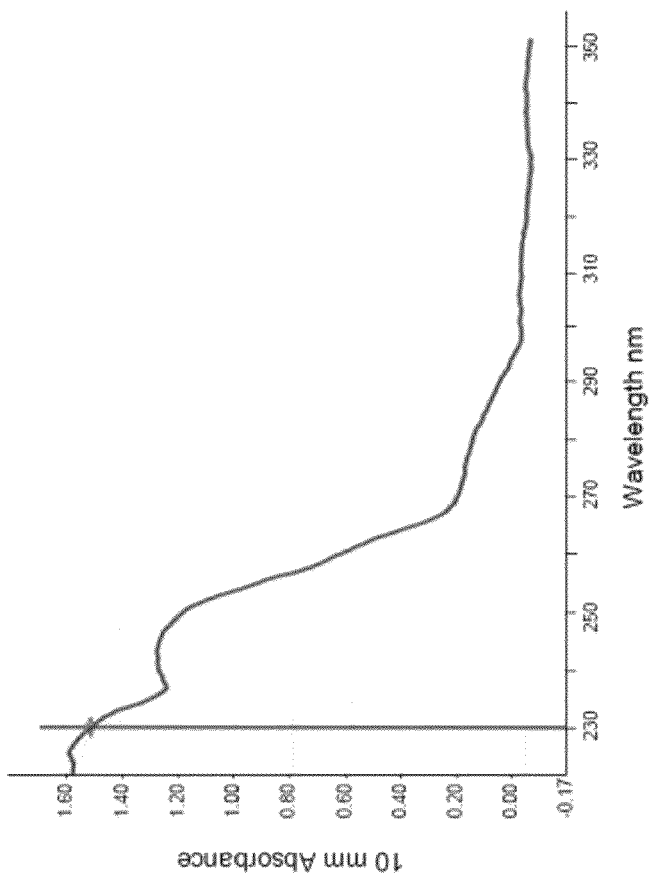
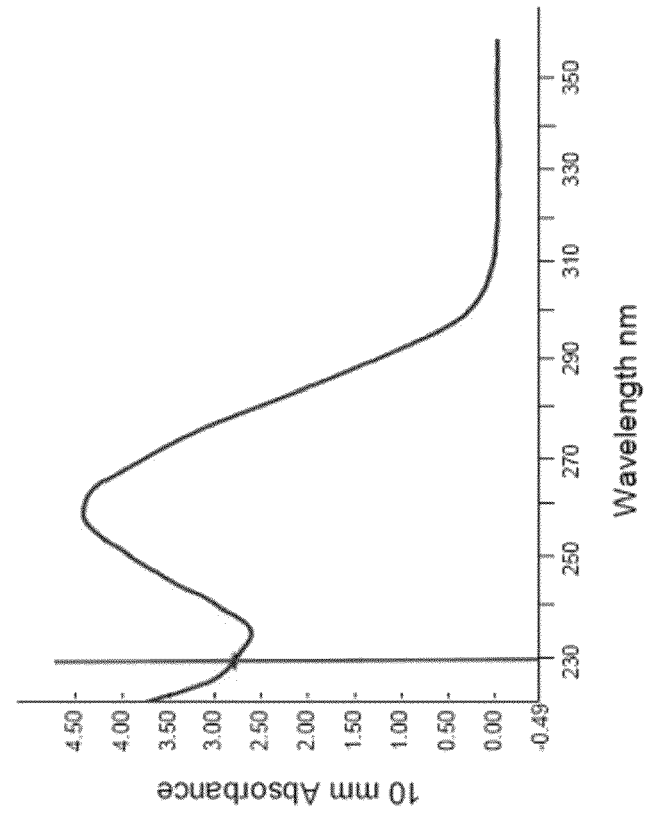
FIGURE 7

SEQUENCE LISTING

```
<160> NUMBER OF SEQ ID NOS: 2

<210> SEQ ID NO 1
<211> LENGTH: 27
<212> TYPE: DNA
<213> ORGANISM: Homo sapiens

<400> SEQUENCE: 1
agatgaagaa tgtgtgtgat ggatgta                                          27

<210> SEQ ID NO 2
<211> LENGTH: 24
<212> TYPE: DNA
<213> ORGANISM: Unknown
<220> FEATURE:
<223> OTHER INFORMATION: a nuclear chromosome encoded gene, amylogenin,
      encoded on both the X and Y chromosome

<400> SEQUENCE: 2
gggctcgtaa ccataggaag ggta                                             24
```

SURFACE MEDIATED SELF-ASSEMBLY OF NANOPARTICLES

CROSS-REFERENCE TO RELATED APPLICATIONS

This application claims priority from Provisional Patent Application Ser. No. 60/896,479, filed Mar. 22, 2007. This application is a continuation-in-part and claims priority from U.S. patent application Ser. No. 11/338,124, filed Jan. 23, 2006, and published as U.S. Patent Application Publication US 2006/0177855 A1 on Aug. 10, 2006. U.S. patent application Ser. No. 11/338,124 claims priority from Provisional Patent Application Ser. No. 60/646,155, filed Jan. 21, 2005 and Provisional Patent Application Ser. No. 60/701,630, filed Jul. 22, 2005. Each of these applications is incorporated herein by reference in their entireties.

FIELD OF THE INVENTION

Matrices for the manipulation of biopolymers, including the separation, purification, immobilization of biopolymers are provided. Systems and methods for three phase chromatography utilizing a liquid phase, a suspended colloidal size solid-phase, and a non-colloidal size solid phase are provided. Systems and methods for two phase chromatography utilizing a liquid phase and a suspended colloidal size solid-phase are also provided.

BACKGROUND

DNA, RNA, immunoglobulins, and proteins are classes of polymeric biomolecules ("biopolymers") of particular importance in modern biochemical and molecular biological methods and processes. Specifically, biopolymers play critical roles in various subcellular processes including the preservation and transmission of genetic information, the production of proteins, and the formation of enzymes.

Due to the importance of these biopolymers in various biological processes, a wide variety of techniques have been developed to physically bind these classes of molecules in order to manipulate them for immobilization, purification, and concentration, etc. For example, various column methods have been developed to bind a biopolymer to a matrix with affinity for that biopolymer, thereby allowing for its immobilization, its separation from contaminating cellular components, its concentration, etc. See, for example, U.S. Pat. No. 5,652,141 for the purification of nucleic acids. Similarly, various bulk separation methods have been developed for the immobilization, separation, or concentration of biopolymers. For example, U.S. Pat. No. 6,718,742 describes the use of magnetic beads comprising a magnetic or paramagnetic particle and an attached ion exchange material capable of binding the biomolecule.

Biopolymer immobilization, separation, concentration or purification is employed across a wide range of commercial applications, including, for example, forensics, pharmaceutical research and development, medical diagnostics and therapeutics, environmental analysis, such as water purification or water quality monitoring, nucleic acid purification, proteomics, and field collection of biological samples. Thus, a need exists for efficient, simplified processing of clinical, environmental and forensic samples, especially for samples containing only nanogram amounts of nucleic acid or protein.

In contrast to conventional nucleic acid extraction and purification methodologies, sub-micron particles or nanoparticles as the solid phase platform for chromatography are provided. One of the preferred nanoparticle materials, kaolin, is used industrially as a filler and bonding agent and is commercially available at high purity and very low cost. The coupling process that has been developed provides surface modified particles (e.g., epoxy-silane coated kaolin) batch-wise in kilogram quantities under conditions where the production cost for the final product is dominated by quality control/quality assurance and packaging.

Various embodiments provide a unique three-phase chromatography based on highly purified, nearly mono-dispersed, ceramic or ceramic-like nanoparticles. These nanoparticles form stable colloidal suspensions in aqueous solution. Since the particles are sub-micron in diameter, they display a large surface area to volume ratio. For example, a milligram of kaolin nanoparticles of 200 nm diameter in colloidal suspension displays a total surface area in the range of 200 $cm^2$, as surface area displayed by approximately $10^{12}$ dispersed nanoparticles. The inter-particle spacing between this number of particles suspended in a milliliter is about one micron, a distance that is less than the distance a 10,000 base pair long DNA molecule or a 1,000,000 Dalton protein would travel by passive diffusion in about one minute. Thus, even at a very low particle-mass density, and in the absence of mixing or convective flow, a 0.1% by weight suspension of these 200 nm diameter nanoparticles are at a per volume concentration such that a targeted biomolecule is never more than "a minute away" from colliding with the surface of a nanoparticle in colloidal suspension. This suggests that, independent of sample concentration, the binding phase for batch chromatography based on these colloidal suspended nanoparticles can be complete within minutes. In addition, due to the small size of these particles, the sedimented pellet volume of this 0.1% suspension of 200 nm kaolin nanoparticles may be as little as about one microliter. These ceramic nanoparticles, having an expansive surface area, provide very useful characteristics as the basis for chromatography, namely an enormous binding capacity per unit mass and the ability to be modified via well-known surface modifying chemistry.

For batch chromatography, the outer surface area is important because it defines the mass and the volume of sample that can be processed at one time. The surface area per unit mass increases with the inverse of the diameter (1/diameter). A comparison can be made between kaolin nanoparticles, having a surface area to mass ratio of about 200 cm per milligram, to smooth, non-porous, 30 micron diameter bead or glass particles, having approximately the same density as kaolin particles and a surface area to mass ratio of about 2 $cm^2$ per milligram. About 100 milligrams of beads would be required to match the surface area of 1 milligram of the kaolin nanoparticles. Assuming that each type of matrix occupies about the same space per unit mass as a pellet, the surface area presented by 1 µL of a 200 nm nanoparticle pellet is equivalent to that of a 100 µL pellet for the standard 30 micron bead. Thus, in this example, a biologically relevant sample would have been concentrated 1000-fold via nanoparticles, but only 10-fold by the 30 µm beads. Alternatively, in terms of binding capacity, a 100 µL pellet of glass beads would have about the same total binding capacity as 1 µL of the nanoparticles.

Rapid development of a broad ranging nano-chromatography platform requires the ability to chemically modify the surface of the ceramic matrix with biomolecule-specific ligands. For these ceramic nanoparticles, surface chemistry has been studied and has been optimized for various applications in the plastics and polymers industry. The present invention utilizes ceramic surface chemistry and biochemical chromatography to develop a flexible repertoire of surface coatings for DNA, RNA, immunoglobulin, and protein applications, each based on the same underlying ceramic nanoparticle matrix.

SUMMARY

Self assembly of nanoparticles onto the surfaces of non-colloidal structures, such as particles (that have dimensions that are greater than 1 µm) or on macroscopic surfaces of other kinds is disclosed. For this discussion, the IUPAC definition of colloidal is being used. The IUPAC definition of colloidal is a particle in which one or more of the dimensions are a micron or less in size, thus non-colloidal means structures or a surface that have dimensions larger than a micron.

Chromatographic compositions and methods using at least two solid phases in suspension, in at least one liquid phase are provided. The first solid phase comprises nanoparticles, or colloidal particles. The second solid phase is generally a non-colloidal, solid phase, including, but not limited to, fibers, filters, and beads. In particular, beads are envisioned which have a ferrite or equivalent core (i.e. magnetic beads) that may be harvested as a pellet in an applied magnetic field. The surface mediated self-assembly of colloidal nanoparticles onto the non-colloidal surfaces results in the flocculation or aggregation of the nanoparticles onto larger structures of about a micron or greater. The nanoparticles for use as a chromatographic agent can be activated with biopolymer binding reagents, allowing the manipulation of biopolymers such as nucleic acids, proteins, immunoglobulins, and carbohydrates. The self-assembly of the nanoparticle onto the surface of a larger substrate or bead is based on the chemistry of oxyanions used to passivate the surface of ceramic or ceramic-like nanoparticles.

In another embodiment, a single solid phase comprising a magnetic nanoparticle is utilized, thereby combining the two solid phases described above into a single solid phase. As described above, the surface of the magnetic nanoparticles can be treated with appropriate reagents for binding to the desired biomolecules. The complex of the biomolecules bound to the magnetic nanoparticles is harvested by the application of a magnetic field. Then the biomolecules are eluted from the nanoparticles.

The nanoparticles are generally solid, non-porous particles with a surface area to volume ratio ($m^2/cm^3$) greater than about 6, where the surface area to volume ratio is determined by multiplying the surface area ($m^2/gram$) by the particle density ($\rho$, in gram/$cm^3$), and a density ($\rho$) greater than about 1.

The surface of the nanoparticles can be modified by using an adaptation of passivation chemistry. Passivation chemistry has been developed to modify the surfaces of metal or corresponding oxides to become less reactive. Such modifications include silane chemistry, oxyanion binding, or the binding of other anions. These chemistries have been adapted to modify the nanoparticle surfaces for biochemical manipulations in such a way that the nanoparticle can both adsorb to a biomolecule (such as DNA) and at the same time interact, via the passivation layer, to a second surface such as a larger bead or structure such as a fiber or membrane.

BRIEF DESCRIPTION OF FIGURES

FIG. 1 also shows RNA adsorption to inosine monophosphate coated zirconium oxide. (See Example 11.)

FIG. 7A is an absorbance spectrum of a human genomic DNA control used as a PCR control shown in lane 7 of FIG. 8 as described in Example 19.

FIG. 7B is an absorbance spectrum of the sample recovered in Example 19 after elution of DNA from the magnetic microparticle-nanoparticle-DNA triplex shown in lane 10 of FIG. 8.

DETAILED DESCRIPTION OF THE PREFERRED EMBODIMENTS

Figure 1:
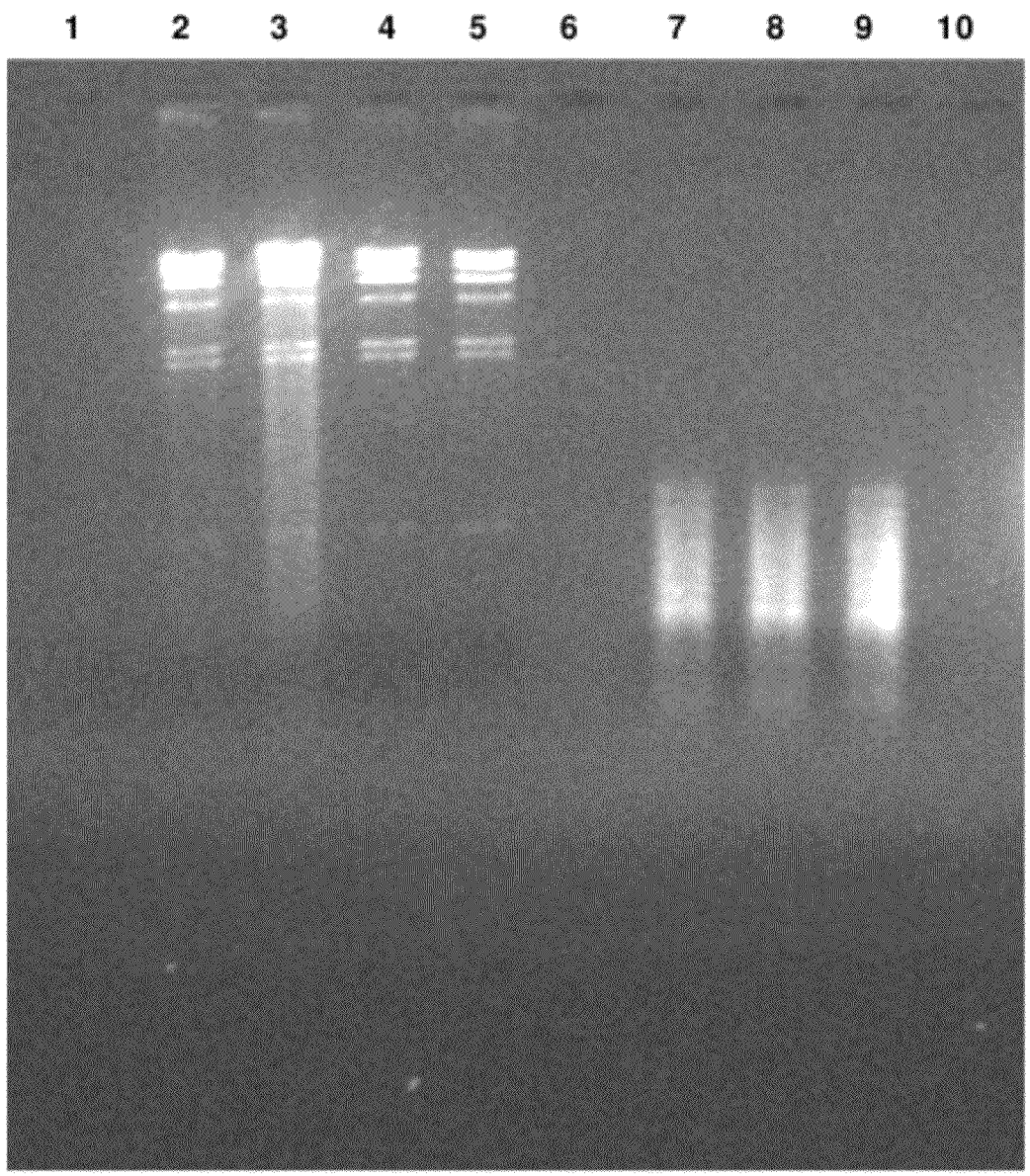
FIG. 1 is an electrophoretic analysis of DNA adsorption using borate treated metal oxides, of aluminum, zirconium, titanium, or tungsten and phosphate/fluoride treated kaolin. (See Example 12).

Materials and methods for surface mediated self-assembly of nanoparticles onto the surface of non-colloidal particles or surfaces are provided. Also provided are chromatographic compositions and methods using at least two solid phases with at least one in suspension in at least one liquid phase. The first solid phase comprises nanoparticles, or colloidal particles. According to the IUPAC definition, colloidal particles generally have a dimension, in at least in one direction, of between about 1 nm to about 1 µm. Due to their small size, colloidal particles in a colloidal suspension generally do not settle out of the mixture spontaneously. The second solid phase is generally a non-colloidal phase, having a dimension of greater that about 1 µm. Examples of a non-colloidal solid phase according to the present invention include, but are not limited to, fibers, filters, and beads. The surface mediated self assembly of colloidal nanoparticles onto the surface of non-colloidal surfaces results in the flocculation or aggregation of the nanoparticles onto the larger non-colloidal structures of about micron size or larger. Having the colloidal nanoparticles with bound biomolecules complexed to the non-colloidal phase allows for easier manipulation of the complex. The nanoparticles for use as a chromatographic agent can be activated with biopolymer binding reagents, allowing the manipulation of biopolymers such as nucleic acids, proteins, immunoglobulins, and carbohydrates.

Generally, the first solid phase, comprising of ceramic or other types of nanoparticles, self assemble onto the surface of a non-colloidal structure which serves as the second solid phase, such as fibers, beads, or filter surfaces. In one preferred embodiment, the second solid phase comprises magnetic beads with dimensions in the range of about 1 micron (µm) to about 100 microns (µm). In one embodiment, the nanoparticle self-assembles to the surface of a magnetic bead, in which the assembly is based on the chemistry of oxyanions bound the surface of ceramic or ceramic-like nanoparticles. In this embodiment, the oxyanion coating serves as a passivation agent, as described in greater detail below and in co-pending U.S. patent application Ser. No. 11/338,124 (6052-006) and PCT Patent Application No. PCT/US2006/028635 (6052-008), incorporated herein by reference in their entireties. Ceramic-like nanoparticles include, for example, metal oxides, metals, clays, silicas or carbides.

The surface of zirconium oxide has been well described, and it can be selectively chemically modified to make it a more acceptable surface for chromatography of various biomolecules. The use of oxyanions, such as phosphate, borate, and carboxylates, as well as the use of fluoride, can render the surface more compatible for chromatography. Such ions can block or interact with the Lewis acid like activity conferred by the zirconium atom at the surface to render the surface of the zirconium oxide more compatible for chromatography.

Oxyanion treated nanoparticles can be used for the manipulation, purification, isolation, and storage of biomolecules, such as DNA, RNA, peptides, and proteins. Partitioning of the nanoparticles from suspension can be carried out by centrifugation as previously described. Alternatively, the treated nanoparticles can be partitioned by using a second, solid-phase. Self-assembly of these nanoparticles onto the surface of a more easily manipulated second surface can also be used to partition the nanoparticles out of suspension. The larger, non-colloidal surface may be stationary, as in the case of a filter, or it may be also be in suspension, as with the use of magnetic beads. Preferably, the surface of the second, non-colloidal material is treated with a coating that enhances a direct interaction with the surface of the nanoparticle, or through the nanoparticle coating. By treating the non-colloidal material in such a manner, the complex of nanoparticles bound to the non-colloidal material preferably does not disassemble during elution of the biomolecule from the surface of the nanoparticle, so that an enriched and concentrated biomolecule preparation can be recovered, free from the stable nanoparticle complex with the non-colloidal surface.

Where chromatographic compositions and methods are used for DNA binding, one embodiment comprises the self-assembly of colloidal phase nanoparticles onto a solid phase surface, such as a micron sized, magnetic particle lattice. Preferably, the nanoparticles are coated with one or more inorganic ions to form a coating that tends not to interact with DNA. The inorganic ion coating on the nanoparticles does, however, enable the binding of the nanoparticles to the polymer-coated magnetic particle lattice. The magnetic particle lattice is preferably coated with a polymer coating, such as poly-alcohols, carboxylates, polysaccharides, and mixtures thereof. The polymer coating on the magnetic particle lattice tends not to interact with DNA. The polymer coating on the magnetic particle lattice does, however, enhance binding of the nanoparticles to the polymer coated magnetic particle lattice. Soluble DNA is driven to adsorb onto the nanoparticle surface through the addition of alcohols, polymers, triaminoalkanes, cationic detergents (such as cetyltrimethylammonium bromide), lithium salts, divalent metallic ions, and the like. The colloidal phase nanoparticles with DNA bound to them then self-assemble onto the magnetic particle lattice, via a direct binding reaction between the inorganic coating on the nanoparticles and the polymer coating on the magnetic particle lattice.

Figure 4:
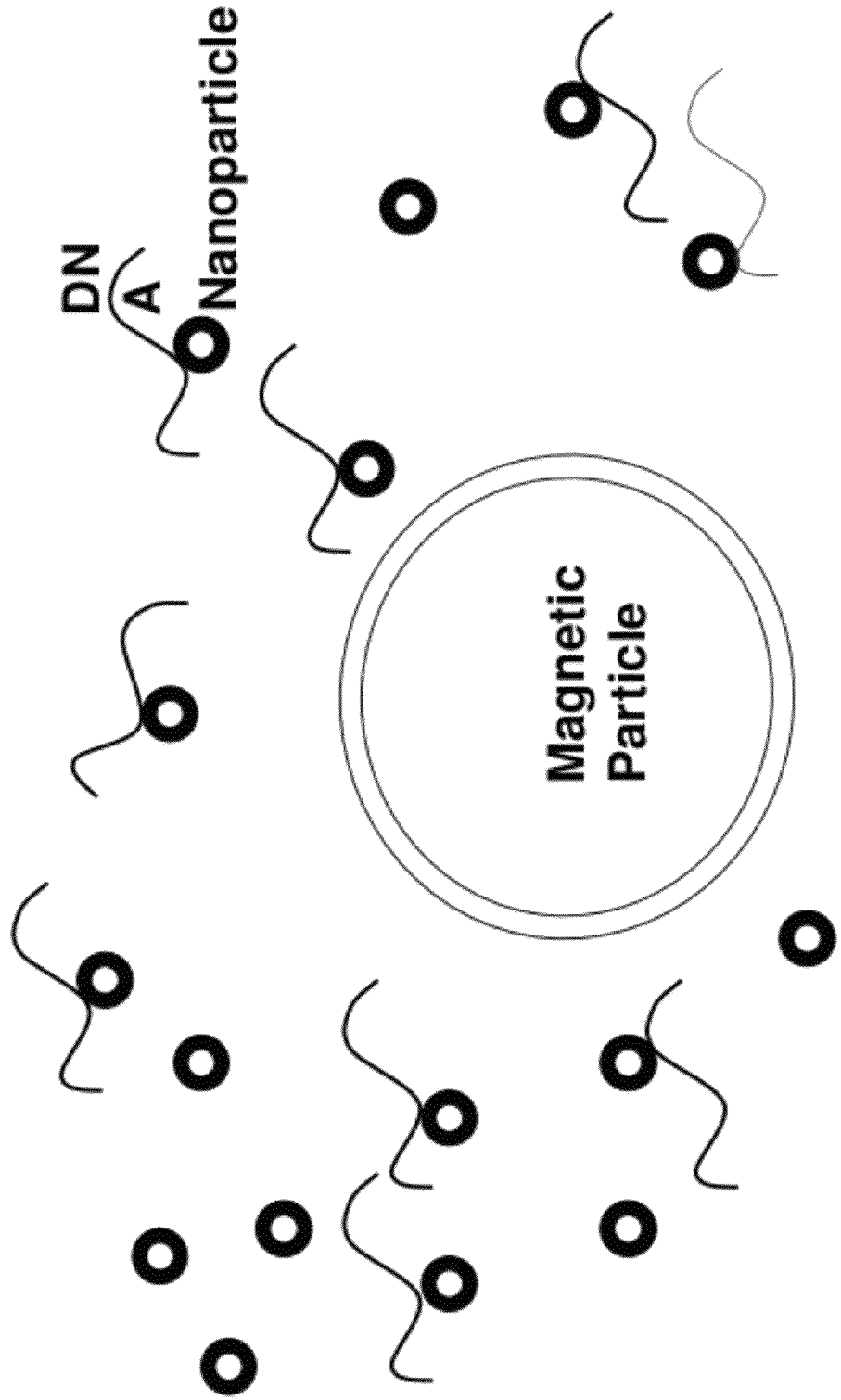
FIG. 4 is a schematic diagram illustrating the available surface area on nanoparticles with adsorbed DNA.
Figure 5:
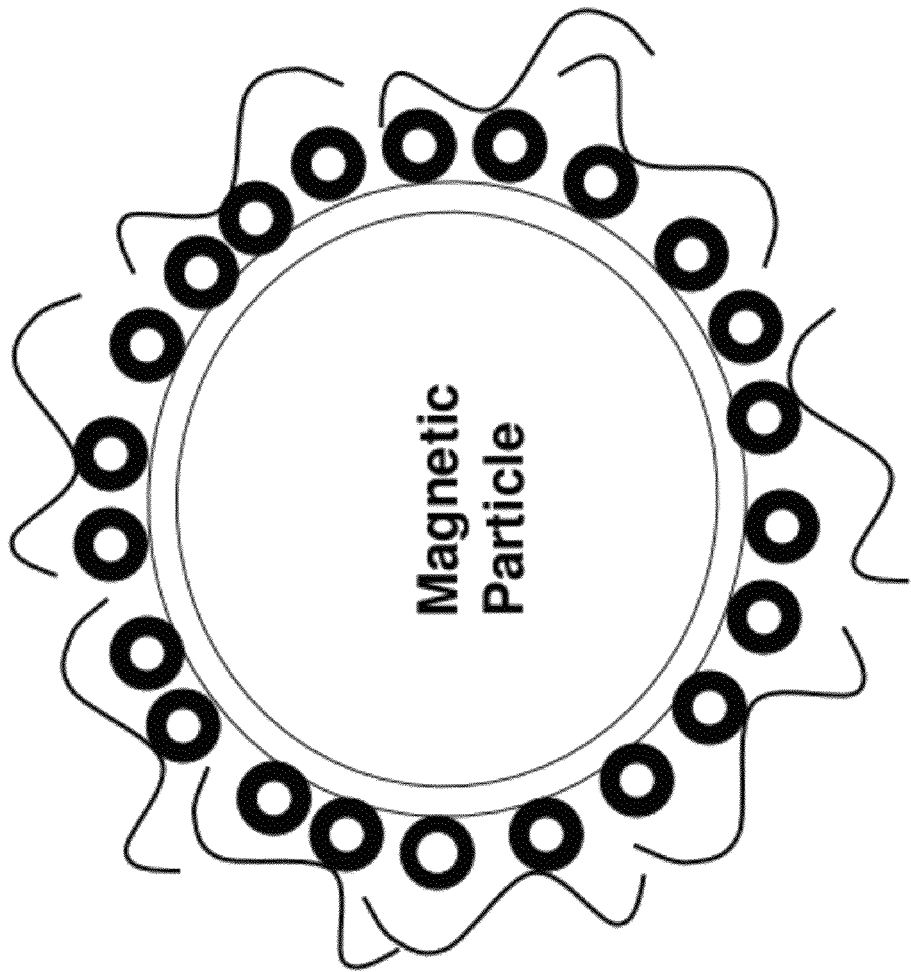
FIG. 5 is a schematic diagram illustrating the self-assembly of DNA-nanoparticle complexes on to the surface of a magnetic particle.

The process of DNA isolation is illustrated schematically in FIGS. 3-6. DNA adsorption onto the nanoparticles occurs rapidly due to the very large surface area of the nanoparticles and the relatively a small distance separating the nanoparticles. (FIG. 3) Considering an example using 40 nm nanoparticles and 20 μm magnetic particles, the DNA adsorbed onto 40 nm nanoparticles only covers about 10% of the nanoparticle surface, and about 90% of the nanoparticle surface remains available to bind to the magnetic particles. (FIG. 4)

Figure 6:
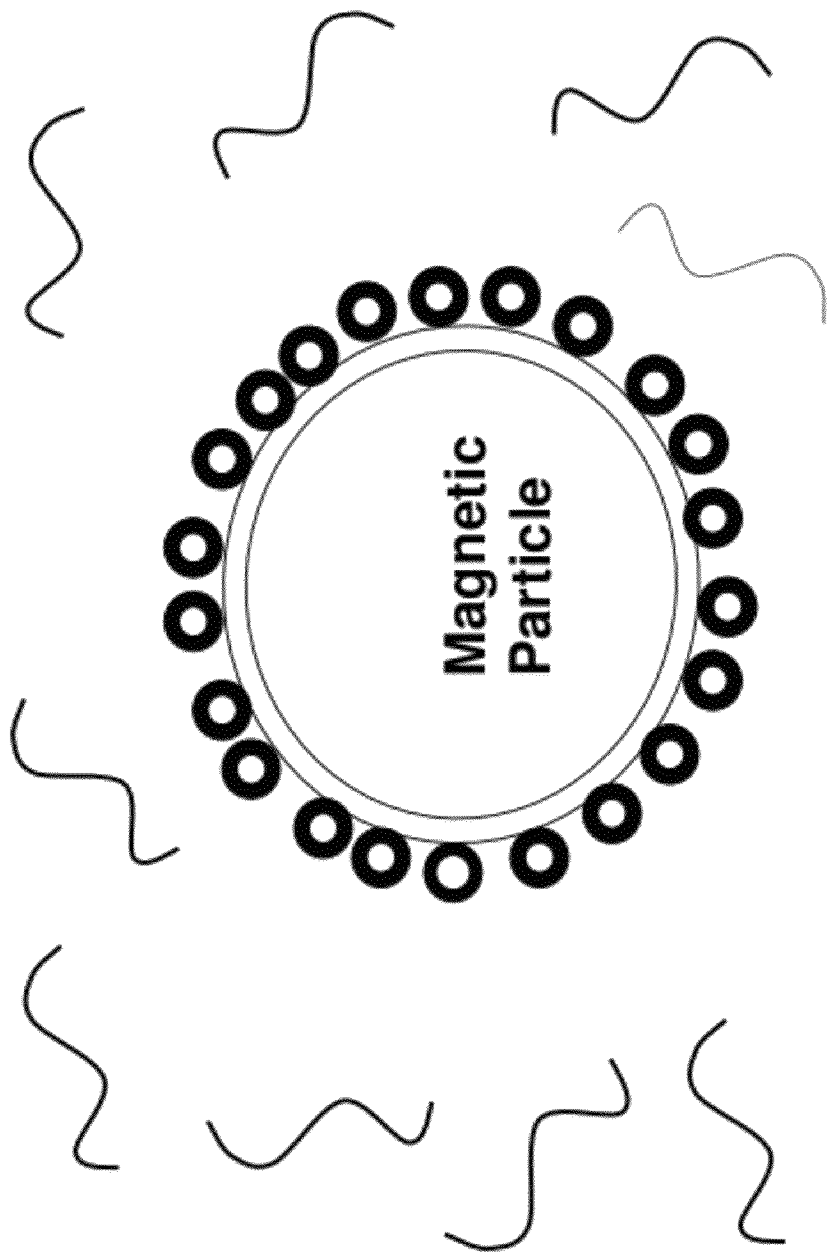
FIG. 6 is a schematic diagram illustrating the dissociation or elution of DNA from the nanoparticles under conditions where the binding of nanoparticle to the magnetic particle is not disrupted.

The DNA-nanoparticle complex tends to self-associate with the 20 μm magnetic particles based on the large remaining DNA-free surface area of the nanoparticle. (FIG. 5) The unused portion of the nanoparticle surface binds to surface coating on the magnetic particles via linkage chemistry between the nanoparticle coating and magnetic particle coating. The particle-particle chemical binding complementarity facilitates the self-assembly between the nanoparticles and the coated magnetic particles. The DNA is then induced to dissociate or elute from the nanoparticles under conditions that do not disrupt the binding of nanoparticle to the magnetic particle lattice (FIG. 6).

The general procedure followed for the nanoparticle-magnetic bead technology is as follows. Nanoparticles are added to a dilute DNA solution. The DNA is allowed to bind to the nanoparticles, usually occurring in the course of minutes. The complementary magnetic particles are then added, and the nanoparticles are allowed to associate with the surface of the magnetic particle, again, usually occurring in the course of minutes. The DNA is then harvested as a DNA-nanoparticle-magnetic particle complex by forming a pellet of the magnetic particles, using a magnetic field. The pellet is then washed to remove contaminants. The DNA is then release from the pellet, preferably under conditions that do not disrupt the nanoparticle binding to the magnetic particle.

In a particularly preferred embodiment, the nanoparticles comprise zirconium oxide or particles coated with zirconium oxide. The preferred nanoparticle size is between about 20 nm to about 300 μm. Preferred nanoparticle surface coatings are borate, or phosphate, or carboxylate. The magnetic particle surface is preferably comprised of dextran, alginate, or polyvinyl alcohol. The magnetic particle size is preferably about 10 μm to about 50 μm. The length of the polymeric coating can range from about 10,000 D to about 10,000,000 D, depending on the depth of the polymeric coating desired.

In an alternate embodiment, a single solid phase comprising magnetic nanoparticles is used. The nanoparticles are treated in a similar manner as described above for the first solid phase. In this embodiment, however, the second solid phase is not required. Once the biomolecule has been allowed to bind to the magnetic nanoparticles, the magnetic nanoparticles are harvested using a magnetic field.

The general procedure followed for the magnetic nanoparticle technology is as follows. Magnetic nanoparticles are added to a dilute DNA solution, for example. (The magnetic nanoparticles can be treated to be used to isolate a variety of biomolecules.) The DNA is allowed to bind to the magnetic nanoparticles, usually occurring in the course of minutes. The DNA is then harvested as a DNA-magnetic nanoparticle complex by forming a pellet of the magnetic nanoparticles, using a magnetic field. The pellet is then washed to remove contaminants. The DNA is then release from the magnetic nanoparticles. Examples of commercially available magnetic particles include SiMAG and fluidMAG particles from Chemicell and TurboBeads such as highly magnetic nanoparticles with a covalent carboxy surface functionality from TurboBeads GmbH.

The term "nanoparticle" refers to a particle having an area to volume ratio of at least about 6 $m^2/cm^3$. Such nanoparticles have a large surface area per unit volume or unit mass, thus offering a large surface area for manipulating a biopolymer.

In view of the large surface area per unit volume or unit mass, the resulting activated nanoparticles of the present invention are able to bind large amounts of biopolymer relative to the unit volume or unit mass of activated nanoparticles used.

Characteristics of the activated nanoparticles include the ability to recover large amounts of biopolymer material, the ability of activated nanoparticles to exist in colloidal form (i.e., to remain suspended in aqueous phase for a long period of time without settling), and, upon binding biopolymers, to form flocculates capable of being concentrated by low-speed centrifugation or by settling under conditions of normal gravity (i.e., "flocculation chromatography") as discussed below, or by controlled flocculation upon the surface of a non-colliodal particle or filter or surfaces of other kinds.

Nanoparticles comprising a variety of substances may be utilized. In general, any material that may be routinely obtained with a largest linear dimension of less than about 1 μm ("sub-micron") and which has the appropriate chemical properties for activation is contemplated as being within the scope of useful nanoparticles. Nanoparticles comprising substances that are sufficiently robust, inert, and inexpensive are considered particularly useful. Nanoparticles including metallic, semi-metallic, and non-metallic nanoparticles, including ceramics, clays, carbon-backboned or composite nanoparticles may be used in various embodiments. One embodiment utilizes nanoparticles composed of kaolin clays. One preferred embodiment of the present invention is directed to clay nanoparticles, and in particular to phyllosilicate clay nanoparticles such as kaolin clay nanoparticles.

In one embodiment, solid-phase, non-porous particles for the manipulation of biomolecules, having a surface area to volume ratio ($m^2/cm^3$) greater than about 6 $m^2/cm^3$, and a density (ρ) equal to about 1 $gm/cm^3$ are used. This would include most organic materials including, for example, colloidal particles made of polystyrene or other plastics, or of cross-linked agarose or of other polysaccharides.

In another embodiment, solid-phase, non-porous particles for the manipulation of biomolecules, having a surface area to volume ratio ($m^2/cm^3$) greater than about 6 $m^2/cm^3$, a density (ρ) greater than about 1 $gm/cm^3$ are used. In another embodiment, the particles have a density greater than about 2 $gm/cm^3$ and less than or equal to about 2.5 $gm/cm^3$ and effective spherical diameters, as determined by two times the Stokes radius, in the range of about 60 nm to about 1000 nm. In yet another embodiment, the particles have a density between about 2.5 $gm/cm^3$ to about 3 $gm/cm^3$ and effective spherical diameters, as determined by two times the Stokes radius, in the range of about 40 nm to about 800 nm. In another embodiment, the particles have a density between about 3 $gm/cm^3$ to about 3.5 $gm/cm^3$ and effective spherical diameters, as determined by two times the Stokes radius, of between about 35 nm to about 400 nm. In another embodiment, the particles have a density between about 3.5 $gm/cm^3$ to about 4 $gm/cm^3$ and effective spherical diameters, as determined by two times the Stokes radius, between about 20 nm to about 700 nm. In another embodiment, the particles have a density between about 4 $gm/cm^3$ to about 4.5 $gm/cm^3$ and effective spherical diameters, as determined by two times the Stokes radius, between about 30 nm to about 600 nm. In another embodiment, the particles have a density between about 4.5 $gm/cm^3$ to about 5 $gm/cm^3$ and effective spherical diameters, as determined by two times the Stokes radius, between about 25 nm to about 550 nm. In another embodiment, the particles have a density between about 5 $gm/cm^3$ to about 5.5 $gm/cm^3$ and effective spherical diameters, as determined by two times the Stokes radius, between about 25 nm to about 500 nm. In another embodiment, the particles have a density between about 5.5 $gm/cm^3$ to about 6 $gm/cm^3$ and effective spherical diameters, as determined by two times the Stokes radius, between about 25 m to about 450 nm. In another embodiment, the particles have a density between about 6 $gm/cm^3$ to about 6.5 $gm/cm^3$ and effective spherical diameters, as determined by two times the Stokes radius, between about 20 nm to about 450 mm. In another embodiment, the particles have a density between about 6.5 $gm/cm^3$ to about 7 $gm/cm^3$ and effective spherical diameters as determined by two times the Stokes radius between about 20 nm to about 400 nm. In another embodiment, the particles have a density between about 7 $gm/cm^3$ to about 7.5 $gm/cm^3$ and effective spherical diameters, as determined by two times the Stokes radius, between about 20 nm to about 400 nm. In another embodiment, the particles have a density between about 7.5 $gm/cm^3$ to about 14 $gm/cm^3$ and effective spherical diameters, as determined by two times the Stokes radius, between about 15 nm to about 300 nm. In yet another embodiment, the particles have a density between about 14 $gm/cm^3$ to about 20 $gm/cm^3$ and effective spherical diameters, as determined by two times the Stokes radius, between about 12 m to about 240 nm.

One embodiment comprises solid-phase nanoparticles for manipulating biomolecules using a colloidal suspension in a liquid phase. The solid-phase nanoparticles are comprised of crystalline, amorphous, or polymer structures, or mixtures thereof. The solid-phase particles are chemically stable under the conditions necessary for particle modification or for biomolecule manipulations. The surface area to volume ratio of the solid-phase particles is greater than about 6 $m^2/cm^3$ and less than about 1000 $m^2/cm^3$. These solid-phase particles preferably have little to no reactivity with the liquid-phase of the colloidal suspension.

In one embodiment, the solid-phase particles are composed of elements comprising metals, semi-metals, or non-metals and their corresponding oxides, carbides, hydroxides, nitrides, phosphates, alloys, ceramic mixtures, clays, glasses, and crystals, and mixtures thereof.

In another embodiment, the solid-phase particles are made of linear or branched polymers with elements from Group III, Group IV, Group V, and Group VI, including those composed of carbon, germanium, or silicon. The solid phase particles can be composed of naturally derived particles of aluminosilicate composition of phyllosilicates such as kaolin or bentonite.

In a preferred embodiment, the solid phase particles have a surface area per gram dry weight of about 6 $m^2$ per gram or greater, and an intrinsic density of greater than about 2 $gm/cm^3$. As the surface area increases, the capacity to bind DNA, RNA, protein, or other biomolecules to the solid matrix also increases. For the nanoparticles, a density greater than that of water ensures that the particles settle and separate from the suspension when desired.

In various embodiments of the present invention, the nanoparticles comprise of clays of the kaolinite, smectic, and montmorillonite classifications, although other clays, such as magnesium silicate clays including bentonite, are also contemplated. The density and geometry of these clays facilitate the formation of a stable suspension. These clays, with a chemical coating, are common components of commercial products such as binders in plastics, glues, and paints. In the preferred embodiments, chemistry for making coated clay particles is adapted to create affinity matrices and surfaces for purifying biopolymers, such as nucleic acids or proteins, from crude or refined samples.

As discussed above, the various embodiments of the present invention contemplate the use of nanoparticles that have been "activated" by a biopolymer binding reagent. A variety of biopolymer binding reagents for use in the activation of nanoparticles to produce activated nanoparticles are also contemplated. In general, it is preferred that such binding reagents are at least bifunctional, having at least one functionality directed to biopolymer binding and another functionality directed to activation of a nanoparticle for binding to a non-colloidal particle or filter or surface. Although these functionalities will often reside in different regions or moieties of the biopolymer binding reagent, biopolymer binding reagents where these functionalities are co-resident in the same area of structure or moiety are also contemplated.

Table 1 indicates the particle size and other characteristics for a series of commercially available nanoparticles that can be used according to various embodiments of the present invention, all of which have the desired specifications that are based on density, surface area per volume, and sedimentation rate predicted by the other two properties. The kaolin nanoparticle product is commercially available through Englehard Corp, now BASF, as the product ASP-G90. ASP is used to designate an aluminosilicate product. Some of the other metal oxides are available from Sigma Aldrich including aluminum oxide (catalog no. 544833), titanium oxide (catalog no. 634662), tungsten oxide (catalog no. 550086), and zirconium oxide (catalog no. 544760).

with surface area dimensions of about 20 $m^2$ per gram or approximately 52 $m^2$ per cubic centimeter, assuming a mean Stokes radius of 200 nm.

Submicron particles are used as the solid phase for the manipulation of biomolecules based on the partitioning of biomolecules to the surface of the non-porous nanoparticles in colloidal suspension. Various chemistries are used to partition the biomolecules from solution phase and to adsorb the biomolecules to a solid phase. Examples include ionic affinity of the nanoparticle surface for the biomolecule; changes in solution conditions that induce the biomolecule to aggregate or adsorb to the solid phase surface; and other changes such as changes in temperature, salt concentration, or pH, and addition of organic solvents, etc. For one trained in the art, these processes of chromatography are generally applicable to the isolation of most biomolecules, such as nucleic acids, proteins, as well as for complex biological complexes such as cells, organelles, and viruses. The examples illustrate the use of solid phase chemistry for biomolecule manipulation using the activated nanoparticles described. These methods are applicable for isolating and manipulating biomolecules including nucleic acids and proteins, as well as other complexes such as cells, organelles, and viruses. In various applications, the biomolecule may be stabilized and stored in

TABLE 1

| Material | Density g/cm$^3$ | <D$_1$>nm exp | m$^2$/g | m$^2$/cm$^3$ | V$_{(2000g)}$ (cm/min) | D$_{min}$ (nm) | D$_{max}$ (nm) | (A/V)$_{min}$ m$^2$/cm$^3$ | (A/V)$_{max}$ m$^2$/cm$^3$ |
|---|---|---|---|---|---|---|---|---|---|
| X$_{ref}$ | 2.0 | 250 | 12 | 24 | 0.46 | 55 | 1,000 | 110 | 6 |
| Kaolin | 2.6 | 200 | 20 | 52 | 0.47 | 50 | 800 | 200 | 13 |
| AlO$_2$ | 2.7 | 43 | 37 | 100 | 0.02 | 40 | 800 | 100 | 12 |
| MgTiO | 3.9 | 50 | 30 | 120 | 0.05 | 35 | 600 | 170 | 10 |
| TiO$_2$ | 4.3 | 50 | 23 | 99 | 0.06 | 30 | 550 | 150 | 9 |
| ZrO$_2$ | 5.9 | 25 | 40 | 240 | 0.02 | 25 | 500 | 240 | 12 |
| WO$_3$ | 7.2 | 40 | 22 | 160 | 0.07 | 20 | 400 | 320 | 16 |
| W | 19.3 | 100 | 7.5 | 150 | 1.34 | 12 | 240 | 1250 | 60 |

In Table 1, the particles tested and described in the Examples are in bold. X$_{ref}$ refers to a preferred embodiment of particle contemplated for use in various embodiments. Other materials are commercially available with the physical characteristics listed. Referring to Table 1, density is expressed in g/cm$^3$. The density is listed for particles tested or otherwise available. <D$_1$>nm refers to average particle diameter as determined by experimental testing. The surface area to mass ratio for the material is expressed in m$^2$/g. The surface area to volume ratio, obtained by multiplying the surface area to mass ratio (m$^2$/g) times the density (g/cm$^3$), is expresses in m$^2$/cm$^3$. V$_{(2000g)}$ (cm/min) refers to the sedimentation velocity calculated for the average particle diameter, <D$_1$>nm, from the Stokes equation, assuming 2000 g. D$_{min}$ (nm) is the smallest average particle diameter that will generate a preferred sedimentation velocity, as defined herein as about 0.1 cm/min at 10,000 g. D$_{max}$ (nm) is the largest particle diameter that will generate a preferred sedimentation velocity, defined herein as about 2 cm/min at 500 g. (A/V)$_{min}$ refers to the surface area to volume ratio, calculated for D$_{min}$ and (A/V)$_{max}$ refers to the surface area to volume ratio calculated for D$_{max}$.

Using properties that can be determined empirically for any type of solid non porous particle, the dimensions for particulate applications can be defined as surface area per volume, as calculated from the surface to mass ratio multiplied by the particle density. Preferred embodiments of the present invention utilize particulate structures whose surface area is equal to or greater than about 6 m$^2$ per cubic centimeter. A particularly preferred embodiment uses kaolin clays either a dry state or a wet state. The examples generally relate to colloidal state, solid phase chromatography using nanoparticles.

Other aspects of the present invention are methods for altering and improving the properties of the activated nanoparticles of the invention via adaptation of metal/metal oxide passivation chemistry. Passivation chemistry generally entails the use of oxyanions for modifying metallic surfaces for corrosion resistance referred to as passivation of metal and metal oxide surfaces. For various embodiments, the nanoparticle matrices contain exposed metal or metal oxide surfaces. The chemistry of passivation, or treating of the nanoparticles with oxyanions, enhances the chromatographic properties of these nanoparticle surfaces, such as improving the reversible binding of biomolecules absorbed to the matrix surface under neutral and mild conditions. In accordance with the present invention, passivation is directed, in particular, to chromatography matrices consisting of nanoparticles and nano-dimensional fibers. The use of passivation chemistry with other chromatographic materials composed of metals or metal oxides can specifically alter or improve their chromatographic surface properties. The composition of these matrices may include clays, such as aluminum silicates, magnesium silicates, or ferric silicates; metals or alloys that contain aluminum, iron, magnesium, zirconium, hafnium, and tungsten; and other metal elements and their respective oxides, either of natural or of synthetic origin. This may include other solid phase matrices that are coated with thin films comprising of metal or metal oxides.

The adapted passivation methods used for various embodiments of the present invention include the binding of oxyanions to metal or metal oxide surfaces. Examples of oxyanions are silicates, borate, phosphate, sulfate, carbonate, arsenate, vanadates, permanganate, molybdate, tungstenate, and chromates. Other ions and compounds that passivate surfaces and can be useful include for example, fluoride ions and chelating compounds based on carboxylic acid moieties, such as EDTA, EGTA, citrate, oxalate, acetate, and formate. Amine or thiol based chelating agents may also behave as surface passivation agents. Examples of amine compounds include diamines, formamide, lysine, and imadizoles, including histidine. Examples of thiols include mercaptans and alkyl thiols such as cysteine. Also useful as passivation agents are phosphate and sulfate derivatives as seen with alkyl sulphones such as sodium dodecyl sulfate or with polysaccharides such as heparin or dextran sulfate. Examples of alkyl phosphones include phosphate detergents as well as phospholipids, phosphorylated polysaccharide, and phosphorylated proteins. These examples are illustrative and not limiting. Oxyanion or oxyanion-like molecules, if passivated onto the surface of a metal, metal oxide, or ceramic surface will, by this process, act as blocking agents to hinder the direct adsorption of a biomolecule like a nucleic acid to these surfaces.

Molecular coatings for solid-phase particles where the coating comprises an epoxy-silane layer can be modified by acid mediated reduction to cis-diols followed by periodate oxidation to form silane bound aldehydes. The aldehydes can link to nucleic acids or proteins. The linkage of these biomolecules can be through reductive amination. The linkage to these biomolecules can also be through phosphates or amines by carbodiimide mediated reactions.

The second layer of molecular coatings for solid-phase particles can be linked with an epoxy-silane layer by epoxy reactive groups such as amines, hydroxyls, or thiols moieties. Through amine linkages the second layer can be selected from polyamines such as linear or branched polymers of polyethylenimine, polylysine, peptides, proteins, chitins, and chitosans, or smaller molecules such as diaminoethane, diaminodipropylamine, spermidine, lysine, or any mixture of the above mentioned molecular species. One preferred polyamine is polyethylenimine (PEI). The polymers can have molecular sizes ranging from about 600 to about 750,000 daltons, in which the polyamine layer can be used as an affinity ligand for anionic molecules or as a molecular linker for other molecular coatings. Through hydroxyl linkages, the second layer can be selected from polymers such as oligosaccharides or polysaccharides, glycoproteins, glycolipids, or synthetic hydroxyl rich polymers such as polyalcohols, dextran sulfates, heparin, polyethylene glycol, to name a few. Through thiol linkages, the second layer can be selected from cysteine containing peptides or proteins, numerous types of mercaptans, thiophosphorylated oligonucleotides, and polynucleotide polymers, for example.

Molecular coatings for solid-phase particles can be constructed by linking a polyamine to a primary layer of epoxy-silane, and utilizing this secondary polyamine as a linker for additional tertiary layers. Such a tertiary layer can be linked either by ionic interaction or by covalent linkage. Covalent linkage chemistries that can be utilized to covalently link a tertiary layer to the epoxy-linked polyamine include anhydrides, divinyl sulfone, hydrazides, or triazines, or by reductive amination, or the halo-alkylation, or the by carbodiimide mediated reactions with hydroxyls, aldehydes or carboxylates, or by the aldehyde mediated reactions of Mannich condensation.

In another embodiment, the molecular coatings for the solid-phase particles comprise an additional layer of molecular coating which is linked between primary amine moieties bound to the particle with aldehyde containing molecular species, by reductive amination or by carbodiimide mediated chemistry. The aldehyde can be produced by oxidation of cis diols with periodate. The oxidized polysaccharide can be from natural sources such as, but not limited to, agaroses, celluloses, chitins, dextrans, heparins, plant starches, glycogens, and synthetic derivatives thereof, or conjugates of polysaccharides with other biomolecules such as glycolipids, or glycoproteins. The glycoproteins can include, for example, proteins such as enzymes, lectins, avidins, and immunoglobulins. The additional layer of molecular coating can be linked by Mannich condensation. Such molecular layers can include steroids, for example, digoxegenin and estrogen (and synthetic derivatives), and dyes such as thymol blue, phenol red, and Coomassie blue.

In another embodiment, a method of affinity chromatography with coated particles in colloidal suspension in which cationic amine containing coatings bind or have a strong affinity for anionic biomolecules such as nucleic acids, phosphorylated proteins, phosphorylated polysaccharides, phospholipids, heparin, heparin analogues, and dextran sulfate is provided. The affinity ligand can bind to ribonucleotides or deoxyribonucleotides in single-stranded, double-stranded, or triple-stranded conformations, or mixtures thereof. The nucleic acids used can be extracted from biological fluids in solutions containing proteases, chaotropic agents, non ionic detergents, and chelating agents such as EDTA. The chaotropic agents may include formamide, guanidinium salts, urea, trichloroacetate salts, and mixtures thereof. The buffers may be chosen from the phosphate, acetate, Tris, MES, MOPS, HEPPS, HEPES, and chloride or sodium salts, in which the pH is adjusted to be within the range of about pH 5 to about pH 9 at buffer concentrations within the range of about 10 mM to about 100 mM. The non-ionic detergents may include Triton X-100, Tween 20, and NP-40 at concentrations within the range of about 0.1% to 2% weight by volume. The proteases can include, for example, subtilisins, proteinase K, chymotrypsin, trypsin, pepsin, papain, and bromelain. The biological samples can include, for example, isolated blood cells (buffy coat or gradient purified), whole blood, serum, saliva, sputum, vaginal/cervical scrapings or washes, mouth/throat swabs or washes, urine, lymph fluids, solid tissues, tissue biopsies, cell samples from tissue culture, microbial cultures, yeast extracts, or plant extracts.

Ceramic surfaces, including the spherical, non-porous ceramic nanoparticles present surface features that readily bind to nucleic acids and to proteins. For example, the literature cites many examples which use such ceramic particles for adsorption chromatography. To reduce or eliminate this intrinsic surface binding, preferred embodiments of utilize surface passivation of nanoparticles with oxyanions to produce a coated surface with very low affinity for most biomolecules. The passivating coating of the nanoparticle allows a biomolecule to be retrieved from the nanoparticle matrix upon rehydration of the matrix without significant adsorptive loss on the nanoparticle surface. For example, one preferred embodiment is directed to the use of nanoparticles made of $ZrO_2$, a substance that ordinarily has a very high affinity for nucleic acids. Other metal oxides, such as tungsten oxide when similarly passivated with borate, these nanoparticle materials can be used as well as a nanoparticle matrix for biomolecule manipulation, such as chromatography.

In a particularly preferred embodiment, the nanoparticles are approximately spherical in shape, ceramic in composition, and have a diameter from about 20 nm to about 1000 nm. The ceramic can be made of metal oxide or aluminum silicates, such as tungsten oxide, zirconium oxide, or kaolin. The surface of these ceramic particles is passivated, or stably treated, with an oxyanion (such as borate, phosphate, sulfate, and citrate) to weaken or eliminate biomolecule interaction with the nanoparticle surface. Such passivated nanoparticles are mixed as a colloidal suspension with the biomolecule and then allowed bind or self-assemble with the second non-colloidal solid phase.

The following non-limiting examples exemplify alternative embodiments of the present invention.

Example 1

Washed Kaolin Nanoparticles

Washed kaolin nanoparticles were prepared for use in adsorption chromatography by first suspending the kaolin (CAS# 1332-58-7) nanoparticles, (Englehard, ASP ULTRAFINE), in N,N, dimethyl formamide (DMF, CAS no. 68-12-2) at a ratio of 0.5 g to 1 g particles (dry weight) to 9 mL DMF. This colloidal suspension was incubated for a minimum of 16 hours. The nanoparticles were washed by a sedimentation-resuspension process by, first, sedimenting the nanoparticles out of suspension by centrifugation at 4000 G for 15 minutes; then resuspending the particles by adding 1 mL of liquid phase (water was used for this process) per 5 grams (dry weight) of particle-sediment, and mixing to form a thick slurry. Next, 9 mL of liquid phase (water) per gram (dry weight) was added to the slurry and mixed to form a confluent nanoparticle suspension. For the washed kaolin particles, for each 10 mL of the nanoparticle suspension, 1 mL of 5 M sodium chloride solution was added and mixed. The nanoparticle suspension was then incubated at room temperature for 12 to 16 hours. These particles were then washed again by the sedimentation-resuspension process, using water as the liquid phase, which was repeated three more times. The final concentration of particles in suspension was adjusted to 50 mg (dry weight) per milliliter in water. This was the suspension of kaolin nanoparticles used for all of the adsorption experiments described in the following Examples.

Example 2

Epoxy Silane Coated Kaolin Nanoparticles in DMF Suspensions

Epoxy-silane coated kaolin nanoparticles were produced by the following method. Acid washed kaolin nanoparticles (Example 1) were sedimented from suspension by centrifugation at 4000 G for 30 minutes and then resuspended in dimethylformamide (DMF) at ratio of 1 gram to 8 mL of DMF. To this 8 mL of the kaolin/DMF suspension was added 2 mL of a 10% solution of 3-glycidoxytrimethoxysilane (epoxy-silane) in DMF and mixed then incubated for minimum of 16 hrs with constant agitation. These epoxy-silane particles were washed by sedimentation-resuspension process (see Example 1), using DMF as the liquid phase, and this process was repeated twice, though the final concentration of epoxy-silane coated particles was 125 mg/mL (dry weight of kaolin particles).

Example 3

PEI—Epoxy Silane Coated Kaolin Nanoparticles in DMF Suspensions

Two types of polyethylenimine (PEI) coated nanoparticles were made by linking PEI polymer kaolin nanoparticle via epoxy-silane linkage. To 8 mL of the suspension of epoxy silane coated kaolin nanoparticles as described in Example 2 was added either 2 mL of a 10% water solution of branched polyethylenimine (PEI) of 750,000 MW (CAS no. 25987-06-8) or 2 mL of a 10% water solution of branched polyethylenimine (PEI) of 25,000 MW (CAS no. 9002-98-6). The PEI/epoxy-silane kaolin suspension were mixed and incubated for a minimum of 16 hours. The PEI-epoxy coated particles were then washed three times by the sedimentation-resuspension process using water as the liquid phase. The final particle concentration for the suspensions of the polyethylenimine-epoxy silane coated kaolin particles was 50 mg dry weight of kaolin nanoparticles per mL of suspension.

Example 4

PCR Analysis of Human DNA Isolated using Kaolin Nanoparticles and PEI-Kaolin Nanoparticles PCR was used to compare and evaluate the DNA capture process using kaolin nanoparticles and PEI-kaolin nanoparticles. These PCR analyses were based on a nuclear chromosome encoded gene, amelogenin, encoded on both the X and Y chromosomes. The primers used were of two sequences. The sequence of the first primer was 5'-AGA TGA AGA ATG TGT GTG ATG GAT GTA-3' (SEQ ID NO:1), and the sequence of the second primer was 5'-GGG CTC GTA ACC ATA GGA AGG GTA-3' (SEQ ID NO:2). Both sequences were derived from the amelogenin sequence in GenBank with accession number AY040206. The PCR product from these two primers is a 558 base pair long fragment. In general, PCR reactions were carried out as follows. The PCR reactions were carried out in a 50 µL volume. The reactions contained 1× Roche PCR Buffer, 1.5 mM $MgCl_2$, 0.4 µM primers, 0.2 mM dNTPs, 0.16 mg/ml BSA, and 0.4 µL of Fast Start Taq at 5 U/µL. The conditions for these PCR tests were as follows. The first step was at 94° C. for 4 minutes. Then there were 35 cycles composed of three steps including 94° C. for 1 minute, followed by 65° C. for minute, and then 72° C. for 1 minute. After these 35 cycles, the reactions were incubated at 72° C. for 7 minutes followed by a holding step at 15° C. until the reactions were stopped. All of PCR results were evaluated by electrophoresis of ⅕ of the reaction volume in agarose gels using a Tris-Borate-EDTA buffer system. The molecular weight control used was the 1 Kb DNA ladder from Invitrogen (catalog no. 15615-016). The PCR controls used were a negative control, a reaction with no added DNA template, and four positive controls with a fixed and known amount of human DNA (Roche Human Genomic DNA catalog no. 1691112) used as PCR templates, generally at concentrations of 10 ng, 1 ng, 0.1 ng and 0.01 ng per 50 µL PCR reaction.

Example 5

Phosphate Treated Kaolin Nanoparticles

The acid washed kaolin nanoparticles were prepared by first suspending the kaolin nanoparticles, Englehardt, ASP G90 (CAS no. 1332-58-7) in de-ionized water at a weight to volume ratio of 1 to 3. This colloidal suspension was incubated for a minimum of 16 hours. The nanoparticles were washed by a sedimentation-resuspension process by first sedimenting the nanoparticles out of suspension by centrifugation at 4000 G for 10 minutes. Then the kaolin nanoparticles were resuspended in water at the same ratio. This process was repeated until the supernatant was clear with no sign of opalescence. The final kaolin pellet was resuspended at a weight to volume ratio of 1 to 3 with water, and an equal volume of 10% sulfuric acid was added to the suspension. This sulfuric acid/kaolin slurry was mixed and incubated at room temperature for 1 to 2 hours. Then the slurry was washed with distilled water by the sedimentation-resuspension process until the pH of the supernatant was the same as the pH of the distilled water. To this suspension, as a 1 to 10 ratio of weight of particles to volume of suspension, was added a $\frac{1}{50}^{th}$ volume of 500 mM NaF, to a final NaF concentration of approximately 10 mM. This suspension was mixed and then subjected to one round of sedimentation-resuspension with distilled water, with the pellet being resuspended in 100 mM $NaH_2PO_4$ at a ratio of 1 to 10 and kept mixing for at least 16 hours. This suspension was subjected to three rounds of the sedimentation-resuspension with 1 mM $NaH_2PO_4$. The particle suspension was stored as this solution until ready for dilution in 1 mM $NaH_2PO_4$ and 10 mM NaF. The final suspension of kaolin nanoparticles was 100 mg to 200 mg particles/mL in a suspension solution of 1 mM $NaH_2PO_4$ and 10 mM NaF.

Example 6

Borate Treated Kaolin Nanoparticles

The acid washed kaolin nanoparticles were prepared by first suspending the kaolin (CAS# 1332-58-7) nanoparticles, Englehardt, ASP G90 in de-ionized water at a weight to volume ratio of 1 to 3. This colloidal suspension was incubated for a minimum of 16 hours. The nanoparticles were then washed by a sedimentation-resuspension process. This process included sedimenting the nanoparticles out of suspension by centrifugation at 4000 G for 10 minutes, resuspending the kaolin in water at the same ratio, and repeating this process until the supernatant were clear with no sign of opalescence. The final kaolin pellet was resuspended at 1 to 3 ratio of weight per volume in water. Then an equal volume of 10% sulfuric acid was added to the suspension. This sulfuric acid/kaolin slurry was mixed and incubated at room temperature from 1 to 2 hours. Then the slurry was washed with distilled water by the sedimentation-resuspension process until the pH of the supernatant was the same as the pH of the distilled water. To this suspension, $\frac{1}{50}$ volume of 500 mM NaF was added at a 1 to 10 ratio. The suspension was mixed and incubated. Then the suspension was subjected to one round of sedimentation-resuspension with distilled water, with the pellet being resuspended in 100 mM borate buffer (1:1 mixture of 100 mM boric acid to 100 mM sodium tetraborate) at ratio of 1 to 10 and mixed for at least 16 hours. This suspension was subjected to three rounds of sedimentation-resuspension with 10 mM borate buffer. The particles were stored in this condition until ready for dilution in 10 mM borate buffer.

Example 7

Borate Treated Zirconium Oxide

Zirconium oxide nanoparticles with an average diameter of about 25 nm (Sigma-Aldrich catalog no. 544760) were suspended at a 1 to 10 ratio (weight to volume) in 50 mM HCl and incubate at room temperature from 1 hour under constant mixing. These particles were washed with distilled water by the sedimentation-resuspension process until the pH of the supernatant was the same as the pH of the distilled water. The nanoparticle pellet was resuspended in 100 mM borate buffer (1:1 mixture of 100 mM boric acid to 100 mM sodium tetraborate) at a ratio of 1 to 10 and mixed for at least 16 hours. This suspension was subjected to three rounds of sedimentation-resuspension with 10 mM borate buffer. The particles were stored in this condition until ready for dilution in 10 mM borate buffer.

Example 8

Inosine Monophosphate Coated Zirconium Oxide

Zirconium oxide nanoparticles with an average diameter of about 25 nm (Sigma-Aldrich catalog no. 544760) were suspended at a 1 to 10 ratio (weight to volume) in 50 mM HCl and incubate at room temperature from 1 hour under constant mixing. These particles were washed with distilled water by the sedimentation-resuspension process until the pH of the supernatant was the same as the pH of the distilled water. The nanoparticle pellet was resuspended in 100 mM NaCl, and inosine monophosphate was added to a final concentration of 2 mg per mL. This suspension was subjected to three rounds of the sedimentation-resuspension process with 10 μg/mL of inosine monophosphate in 100 mM NaCl. The particles were stored in this condition until ready for dilution in 10 μg/mL of inosine monophosphate.

Example 9

Adsorbing DNA onto Nanoparticles Using Alcohols

In this example, LiCl or NaCl is added to a 0.5 M concentration to a DNA containing solution. Then nanoparticles passivated with phosphate or borate (See Examples 5 and 7) are added at a weight to volume ratio ranging from about 0.001% to about 1% to form a suspension. To this DNA sample-nanoparticle suspension two volumes of either ethanol or isopropanol are added, mixed, and incubated for 10 to 30 minutes at room temperature. The particles are pelleted by centrifugation at forces ranging from about 500 to about 10,000 G. The supernatant is removed, and the particles are washed in an alcohol solution of about 40% to 100% ethanol or isopropanol, with or without NaCl or LiCl at a 100 mM to 200 mM concentration. The particles are sedimented under centrifugation as mentioned above and air-dried. The DNA can be eluted in a particle to volume ratio that can generally range from about 1:10 to as great as about 1:20000, with a typically range from about 1:200 to about 1:1500. The temperature of elution generally ranges from room temperature to about 55° C.

Example 10

Purification of Nucleic Acids Using Phosphate or Borate Treated Kaolin Particles or Borate Treated Metal Oxide Particles for Adsorption Chromatography Based on Cetytrimethylammonium Bromide The starting material is a 500 μL DNA sample containing 20 mM Tris (pH 7 to 8), 2 mM EDTA, and 700 mM NaCl. 5 to 50 μL of 10% cetyltrimethylammonium bromide (CTAB) is added and mixed. To this DNA preparation, 10 μL of phosphate-treated kaolin (Example 5), borate treated kaolin (Example 6), or the borate treated metal oxides (Example 7) are added at a concentration of 12.5 mg/mL and mixed by pipetting or by vortex-mixing. This DNA preparation is diluted by adding 500 μL to 700 μL of water, mixing by vortex, and incubating for 10 to 30 minutes with occasional mixing at a temperature between 4° C. to room temperature.

The suspension is centrifuged for 4 minutes at 2000 G, and the supernatant is carefully removed from the pellet. To this pellet, 500 µL of 500 mM LiCl in 50% ethanol is added, and the pellet is fully resuspended in this solution. This suspension is centrifuged for 2 minutes at 2000 G. The pellet is resuspended in a 500 µL solution of 700 mM LiCl, 10 mM Tris (pH 8), 1 mM EDTA, and 10 mM borate buffer (pH 8). To this particle eluate, 500 µL of ethanol is added, and the suspension is incubated for 30 minutes. Then the suspension is centrifuged for 4 minutes at 2000 G. The pellet is washed in 50% ethanol-100 mM NaCl and centrifuged for 2 minutes at 2000 G. The supernatant is carefully removed from the pellet, and the pellet is allowed to air dry for 10 minutes. The DNA is eluted from the nanoparticles by adding at least 10 µL to 150 µL of an elution buffer consisting of 2 mM phosphate buffer, 10 mM Tris, 4 mM acetic acid, 0.1 mM EDTA, and 20 mM NaCl. This is allowed to incubate for at least 5 minutes and then mixed to resuspend the particles. The suspension is then allowed to incubate between 10 minutes to one hour. The particles are sedimented from the eluate, and the eluate is transferred to a new tube, and the pellet is discarded.

Example 11

Purification of rRNA Using Inosine Monophosphate Coated Zirconium Oxide Particles E. coli rRNA adsorption to inosine monophosphate coated zirconium oxide is shown in FIG. 1. The inosine monophosphate (IMP) coated zirconium oxide nanoparticles were made according to Example 8. For each of lanes 7-9, the adsorption process used was to add 2 µg of rRNA from E. coli dissolved in 5 mL to 50 µL of a solution containing 0.1% sodium lauroyl sarcosine, 1.0 M LiCl, 20 mM Tris-OH/Tris-HCl (pH 8), and 2 mM EDTA. The sample in lane 8 was augmented with 20% formamide, and the sample in lane 9 was augmented with 600 mM guanidine hydrochloride (Gu-HCl). To this was added 20 µL of a IMP-$ZrO_2$ nanoparticle suspension (~1 mg). The suspension was incubated for 30 minutes and then centrifuged for 4 minutes at 2000 G. The supernatants were removed from the pelleted particles. These particles were resuspended in 200 µL of 1× binding solution containing 0.1% sodium lauroyl sarcosine, 0.5 M LiCl, 10 mM Tris-OH/Tris-HCl (pH 8), and 1 mM EDTA, (Lane 7). The suspensions were then subjected of centrifugation for 2 minutes at 2000 G, and the pellets were retained while the supernatants were discarded. The pellets were then resuspended in an elution buffer of 50% formamide, 10 mM Borate buffer (pH 9.2), 10 mM Tris, 4 mM acetic acid, 20 mM NaCl, and 2 mM phosphate buffer, and were incubated for 30 minutes. Half of the eluates were analyzed in a 1% agarose TBE gel as shown in FIG. 1.

Example 12

DNA Adsorption Using Borate Treated Metal Oxides of Aluminum, Zirconium, Titanium, or Tungsten, and Phosphate/Fluoride Treated Kaolin This example is an analysis of DNA adsorption using borate treated metal oxides of aluminum, zirconium, titanium, or tungsten, and phosphate/fluoride treated kaolin. The DNA samples used were HinD III restriction endonuclease digests of Lambda phage DNA. In FIG. 1, Lanes 1 through 5 contain one half of the Lambda/HinD III DNA adsorbed to the various nanoparticles used. Lane 1 contains half of the DNA eluted from borate treated aluminum oxide nanoparticles (~45 nm diameter). Lane 2 contains half of the DNA eluted from borate treated titanium oxide nanoparticles (~80 µm diameter). Lane 3 contains half of the DNA eluted from borate treated tungsten oxide nanoparticles (~25 nm diameter). Lane 4 contains half of the DNA eluted from borate treated zirconium oxide nanoparticles (~25 nm diameter). Lane 5 contains half of the DNA eluted from phosphate-fluoride treated kaolin nanoparticles (~200 nm diameter). The preparation of the phosphate/fluoride treated kaolin and the borate treated metal oxides is described in Examples 5, and 7. Under the conditions used for this alcohol adsorption, the borate treated aluminum oxide did not perform as well as the other particles.

Lanes 7-9 of FIG. 1 are described in Example 11. Lanes 6 and 10 of FIG. 1 were blank.

Example 13

Figure 2:
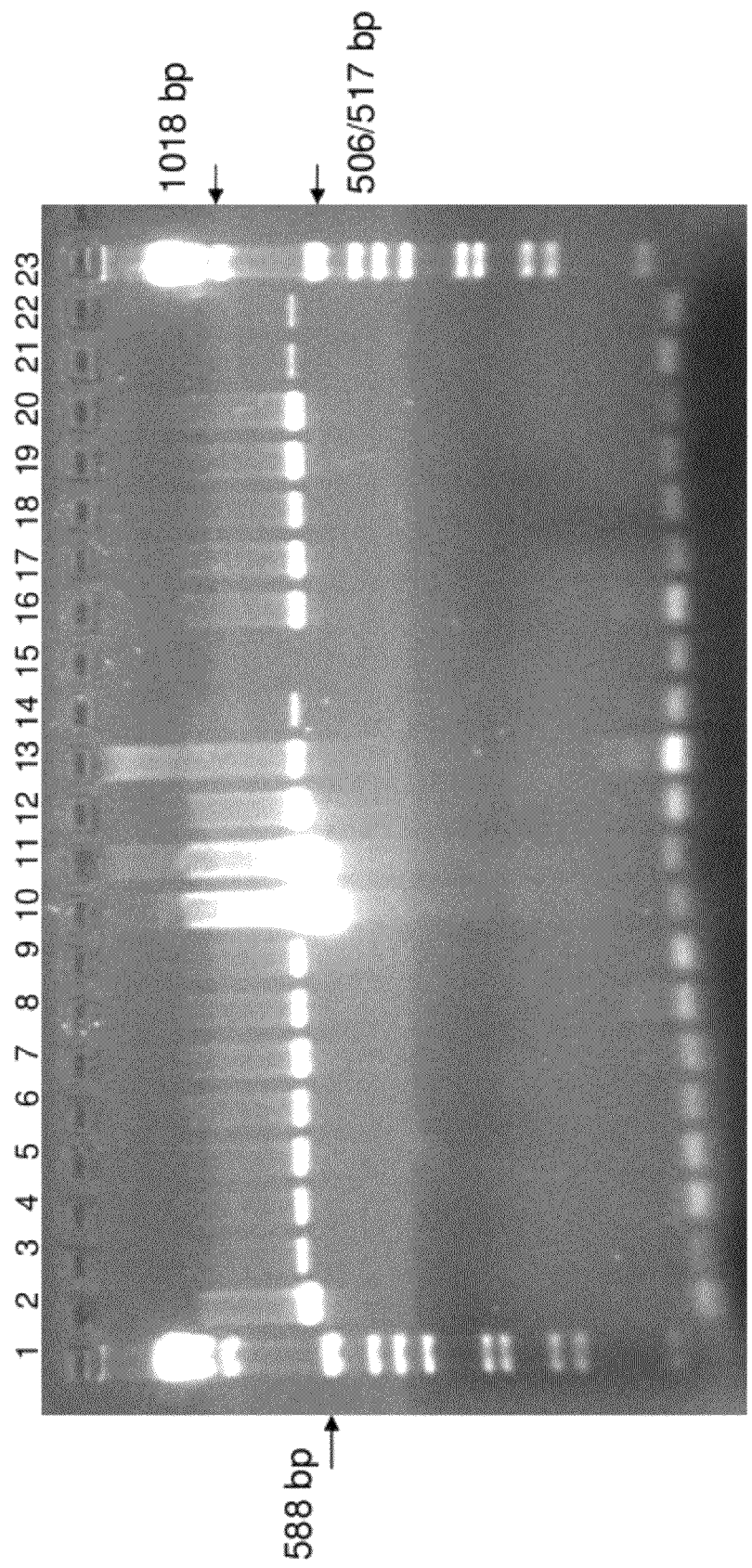
FIG. 2 is an electrophoretic analysis of PCR products generated from the DNA extracted from whole blood using alkaline buffered sodium dodecyl sulfate (SDS), sodium lauroyl sarcosine, guanidinium hydrochloride, and alkaline protease. The PCR amplicon is a 558 bp fragment from human amylogenin gene.
Figure 3:
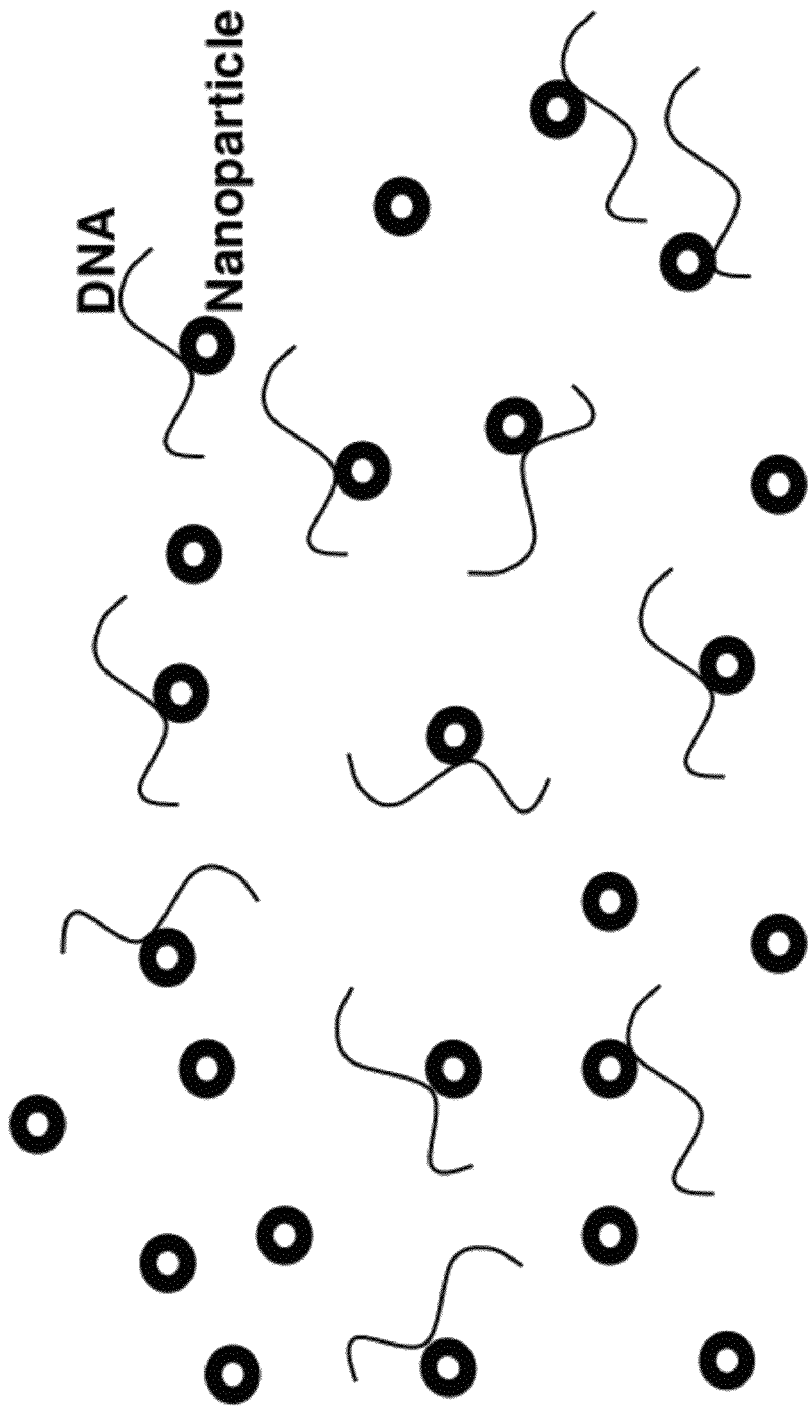
FIG. 3 is a schematic diagram illustrating DNA adsorption onto nanoparticles.

Purification of DNA from Whole Blood using Alkaline Buffered Sodium Dodecyl Sulfate (SDS), Sodium Lauroyl Sarcosine, Guanidinium Hydrochloride, and Alkaline Protease The PCR reaction products from this DNA extraction are shown in FIG. 2. DNA samples were suspended the in an alkaline extraction buffer consisting of 10 mM CAPS (3-(Cyclohexylamino)-1-propanesulfonic acid sodium salt,) 10 mM sodium carbonate, 10 mM EDTA, 100 mM NaCl, sodium lauroyl sarcosine at 0.01% (wt/wt), and sodium dodecyl sulfate (SDS) at 1% (wt/wt). The sample was incubated at 56° C. for 10 minutes. Then 50 µL or 0.665 U of protease from Bacillus species (Sigma-Aldrich P3111, SAVINASE®, Subtilisin, serine endoprotease) was added to each extract. The extract with protease was incubated at 56° C. for 90 minutes up to overnight (about 16 hours), depending on the sample. The total volume of whole blood sample for did not exceed 20% of the volume of the protease treatment. For samples that were 5 µL or less, the digest volume with the sample was 500 µL and the protease concentration was 1.3 U/mL. For samples that were 200 µL, the digest volume was 800 µL, and the protease concentration was 0.83 U/mL. After the protease digest, guanidinium hydrochloride (GuHCl) was added to 0.9 M and sodium lauroyl sarcosine was added to a concentration of 1% (wt/wt). The extract solution was incubated at 56° C. for 5 minutes, then equilibrated to room temperature for 10 minutes. The extract was centrifuged at 10,000 G for 10 minutes to pellet the remaining suspended solids, cellular material, and solids that flocculated due the interaction of the added guanidinium hydrochloride. The clarified supernatant was transferred to a new tube and each of the following were added in order with mixing between each addition: 125 µg of phosphate/fluoride treated kaolin nanoparticles (Example 5), LiCl to 0.5 M, and 1 volume of isopropanol (to a final concentration of 50% by volume). The extract with the kaolin-nanoparticle suspension was incubated at room temperature for about 30 minutes, then subjected to a 4,000 G centrifugation for 5 minutes, causing the kaolin nanoparticles to sediment to a dense pellet. The supernatant was removed from the pellet and discarded. The pellets (and tube) were rinsed with an ethanol-saline solution (50% ethanol by volume with 0.15 M sodium chloride). The kaolin nanoparticles were pelleted by centrifugation for 2 minutes at 4,000 G, and the supernatant was removed from the pellet and discarded. The pelleted particles were air dried for about 10 minutes. Then an elution buffer consisting of 10 mM sodium borate, 0.1 mM EDTA, and 0.001% polyethylene glycol sorbitan monolaurate (TWEEN-20®, polyoxyethylene (20) sorbitan monolaurate )

(pH~9.5) was added to the pellet. The pelleted nanoparticles were dispersed into this elution buffer by first heating at 56° C. for 5 minutes, then agitating the pellet by vortex-mixing to disperse the pellet to a confluent suspension, and then heating at 56° C. for an additional 30 minutes. After this step, the spent-kaolin nanoparticles were removed by centrifugal sedimentation, and DNA enriched supernatants were transferred to a new tube.

For PCR analysis, an equivalent blood sample was added to each reaction. For some samples, the DNA eluate was diluted to reflect the difference in sample size, from 0.05 µL of blood to 200 µL of blood. Referring to FIG. 2, in lanes 2 and 3, each sample contained 0.05 µL of whole blood. The protease extraction was in 500 µL for 90 minutes, and the DNA was eluted in 15 µL. The 25 µL PCR reactions used 3 µL of DNA extract. For lanes 4 and 5, each sample contained 0.1 µL whole blood. The protease extraction was in 500 µL for 90 minutes, and DNA was eluted in 15 µL, which was diluted 2×, and 3 µL of this dilution was used for the 25 µL PCR reaction. For lanes 6 and 7, each sample contained 0.5 µL whole blood, and the protease extraction was in 500 µL for 90 minutes. DNA was eluted in 15 µL which was diluted 10×, and 3 µL of this dilution was used for the 25 µL PCR reaction. For lanes 8 and 9, each sample contained 1.0 µL whole blood, and the protease extraction was in 500 µL for 90 minutes. DNA was eluted in 15 µL, which was diluted 20×, and 3 µL of this dilution was used for the 25 µL PCR reaction. Lanes 10 and 15 were the PCR controls consisting of sample purified human DNA. The amounts of DNA in the control lanes was 10 ng in lane 10, 1 ng in lane 11, 0.3 ng in lane 12, 0.1 ng in lane 13, 0.01 ng in lane 14, and no DNA in control lane 15. For lanes 16 & 17, each sample contained 5.0 µL whole blood, and the protease extraction was in 500 µL for 90 minutes. DNA was eluted in 25 µL, which was diluted 60×, and 3 µL of this dilution was used for the 25 µL PCR reaction. For lanes 18, 19 and 20, each sample contained 200 µL of whole blood, and the protease extractions were each in 800 µL. The protease extraction times were 90 minutes for lane 18, 120 minutes for lane 19, and 240 minutes for lane 20. Each of the DNA preparations were eluted in 75 µL, and each were diluted 800×, and 3 µL of each dilution was used for 25 µL PCR reactions. Lanes 21 and 23 were extracts from 6 mm paper disks soaked in whole blood and stored under ambient condition for 3 years. Lane 21 used a sample extracted from one disk, and lane 22 used a sample extracted from three disks. The protease extractions were each in 500 µL for overnight, and the resulting DNA preparations were eluted in 25 µL. The DNA eluate of the lane 21 sample was diluted 260×, and the DNA eluate of lane 22 was diluted 780×. For each, 3 µL of the diluted eluate was used in a 25 µL PCR reaction. For lanes 1 and 23, 1 microgram of DNA molecular weight ladder was loaded per lane.

Example 14

Self Assembly of Nanoparticles onto a Non-Colloidal Magnetic Bead Surface for DNA Isolation Using Borate as the Oxyanion General conditions for self assembly of nanoparticles onto a non-colloidal surface for DNA isolation start with DNA at a concentration of less than about one microgram per milliliter and the nanoparticle surface area being in the range of about 20 cm$^2$ to about 400 cm$^2$ per milliliter of nanoparticle suspension. Under these conditions, approximately 10% or less of the nanoparticle surface would be occupied by adsorbed DNA, with the remaining 90% of the nanoparticle surface exposing the oxyanion capable of interacting with the surface of a magnetic bead. Where the nanoparticle oxyanion is borate, the magnetic bead is coated with polymers of polyalcohols or polysaccharides so that the borate ions bound to the nanoparticle surface can also bind to the hydroxyl groups displayed on the magnetic bead coatings. If the borate surface contacts a number of hydroxyl groups of the polyalcohol coating of the magnetic bead, the combined affinity of the two surfaces would be much greater in buffers that would be useful to elute the DNA from the nanoparticle surface. Due to the affinity of the nanoparticles to the magnetic bead under such conditions, the nanoparticles remain bound to the surface of the magnetic bead while the adsorbed DNA is released.

Partitioning of the nanoparticles from suspension is carried out through the attachment of the nanoparticles to the surface of the magnetic beads. Then a magnetic field is applied to the magnetic beads (with the nanoparticles self-assembled on the surface). The magnetic beads are attracted to the magnetic field, removed from suspension, concentrated, and thus partitioned from the suspension. For this application, in order to coat the magnetic bead with polyalcohol or polysaccharide, one method is to start with magnetic beads with an epoxy activated surface. Then the poly alcohol or polysaccharide is bound to the surface through the ether linkages that are formed by reaction of alcohol moieties within the polymer and the epoxide-coated surface. If desired, additional polymers can be added through this linkage or the bound polymer can be cross-linked through bis-epoxide chemistry such as with ethyleneglycoldiglycidylether, an epoxy compound commonly used to cross-link polysaccharides and poly alcohols.

Example 15

Self Assembly of Nanoparticles onto a Non-Colloidal Surface for DNA Isolation Using Phosphate as the Oxyanion This example is carried out using a method similar to that in Example 14 except that the nanoparticle oxyanion coating used is phosphate, and the magnetic bead coating is a polycarboxylate, such as alginic acid. In this case, the nanoparticle self assembly reaction is mediated by the addition of a divalent cation such as $Ca^{2+}$. The addition of $Ca^{2+}$ in the form of the chloride salt into the suspension containing the phosphate coated nanoparticles (with adsorbed DNA bound to them) and alginic acid coated magnetic particles, causes the nanoparticles to self assemble onto the surface of the magnetic beads at $Ca^{2+}$ concentrations of less than about 20 mM. The self assembly is driven by the co-chelation of the $Ca^{2+}$ by the nanoparticle bound phosphate and the alginic acid carboxylate.

Another way to cause this self assembly is to first saturate the alginic acid carboxyl groups with a divalent cation, such as $Ca^{2+}$, then to add the $Ca^{2+}$ saturated magnetic particles to the nanoparticle suspension. The result being linking of the nanoparticles to the magnetic bead calcium algenate coating.

Example 16

Self Assembly of Nanoparticles onto a Non-Colloidal Surface for DNA Isolation Using Borate This example is carried out in a manner similar to example 14 in chemical linkage, but the poly-alcohol coating of the magnetic particle is saturated with borate and the nanoparticles are also coated with borate. Self assembly is mediated by the addition of polyvinyl alcohol or a polysaccharide at a low enough concentration to cross link the magnetic bead to the borate coated nanoparticle. This assembly occurs under conditions where the free polymer is at limited concentration, i.e. at a concentration where preferably no surface is individually saturated with the soluble poly-alcohol.

Example 17

Self Assembly of Nanoparticles onto a Non-Colloidal Surface Using Monophosphate Nucleotide Coated $ZrO_2$ Nanoparticles In this example, zirconium oxide nanoparticles are coated with a monophosphate nucleotide, such as inosine monophosphate (IMP) or uridine monophosphate (UMP). (See Example 8.) The magnetic beads have 5'- or 3'-tethered poly-A attached to the surface. After the solution phase DNA binds to the nanoparticle surface, the poly-A (or poly-dA) coated magnetic beads are added under conditions that induce the poly-A nucleotides to anneal to the monophosphate nucleotide coated surface of the nanoparticles. Similarly, this can be carried out using any known complementary base-pair structures.

Example 18

Self Assembly of Nanoparticles onto a Non-Colloidal Surface Using Thiophilic Structures In this example, the use of thiophilic structures are used for self assembly. Both the nanoparticle and the magnetic bead surface are coated with a thiophilic structure. One example is divinyl sulfone coupled with mercaptoethanol, or mercaptopropanol, or a similar type linkage. Using thiophilic structures, the self assembly can be mediated by the addition of tryptophan, or phenylalaline, or tyrosine containing peptides that can be interspersed with serine and glycine residues. The assembly is mediated, for example, by the affinity of the thiophilic structure for the trytophan residues of the free polymer. As mentioned above, the polymer is added at limited concentrations to mediate the linkage of the nanoparticles to the surface of magnetic particle. This format is especially useful for the isolation of immunoglobulin proteins.

Example 19

Self Assembly of DNA-Nanoparticle Complexes onto a Magnetic Bead Surface for DNA Isolation High molecular weight human genomic DNA (Roche Diagnostics, 11 691 112 001, 100 μg/500 μL) was resuspended at a concentration of 200 ng/100 μL in distilled water and dispensed into multiple RNase/DNase-free microfuge tubes. The volume of each sample was raised to 500 μL with pH 8.0 1× TE Solution. A sarcosyl solution containing 0.015% (100 mM) calcium chloride was added to the DNA solution. The detergent serves as a blocking agent to prevent DNA adsorption to non-specific surfaces and the divalent cation is thought to serve as a "bridge" between the surface moieties of the nanoparticles and the magnetic beads. 10 μL of borate treated kaolin nanoparticles, as described in Example 6 (Argylla, 100 00 00), and a significant volume of isopropanol were added to the samples. The samples appeared milky upon addition of the nanoparticles, as expected. DNA was allowed several minutes to complex with the nanoparticles.

Magnetic carboxylate-modified particles (Sera-Mag Magnetic Carboxylate-Modified Microparticles, Seradyn, Inc., 24152105050250) were introduced at twice the volume of the nanoparticle suspension. Several minutes were allowed for self-assembly of the DNA-nanoparticle-magnetic microparticle triplex in solution. Samples containing DNA, nanoparticles, and magnetic microparticles were clouded and brown in color. The self-assembly of DNA-bound nanoparticles onto the surface of the larger magnetic microparticles was evidenced by distinct partitioning to the tube walls closest to the magnetic field provided by a FlexiMag Magnetic Separator (Spherotech Inc., FMS-1000). The samples had a brown, partitioned residue and a clear, colorless liquid phase. The liquid phase was withdrawn, and the triplex particles were washed with a dilute ethanol-containing solution. The washed triplex conjugates were repartitioned in the magnetic separator, and the clarified wash solution was withdrawn from each tube.

DNA was eluted with a 10× elution buffer containing EDTA, TWEEN-20® (polyoxyethylene (20) sorbitan monolaurate), sodium tetraborate decahydrate, and sodium phosphate (Argylla, 300 00 01). 100 μL of eluate was collected. The DNA collected was analyzed using a NanoDrop ND-1000 full-spectrum UV/Visible spectrophotometer and subjected to PCR for amplification of six genomic target sequences. FIG. 7A is the absorbance spectrum of the human genomic DNA control used as a PCR control shown in lane 7 of FIG. 8. FIG. 7B is an absorbance spectrum of a DNA sample recovered after elution of DNA from the magnetic microparticle-nanoparticle-DNA triplex. The high absorbance at 230 nm in FIG. 7B is likely due to the presence of salts in the eluate. The shoulder at 260 nm reflects the DNA content of the sample. The DNA sample shown in FIG. 7B was used as the template for the PCR reaction in lanes 9 and 10 of FIG. 8.

Figure 8:
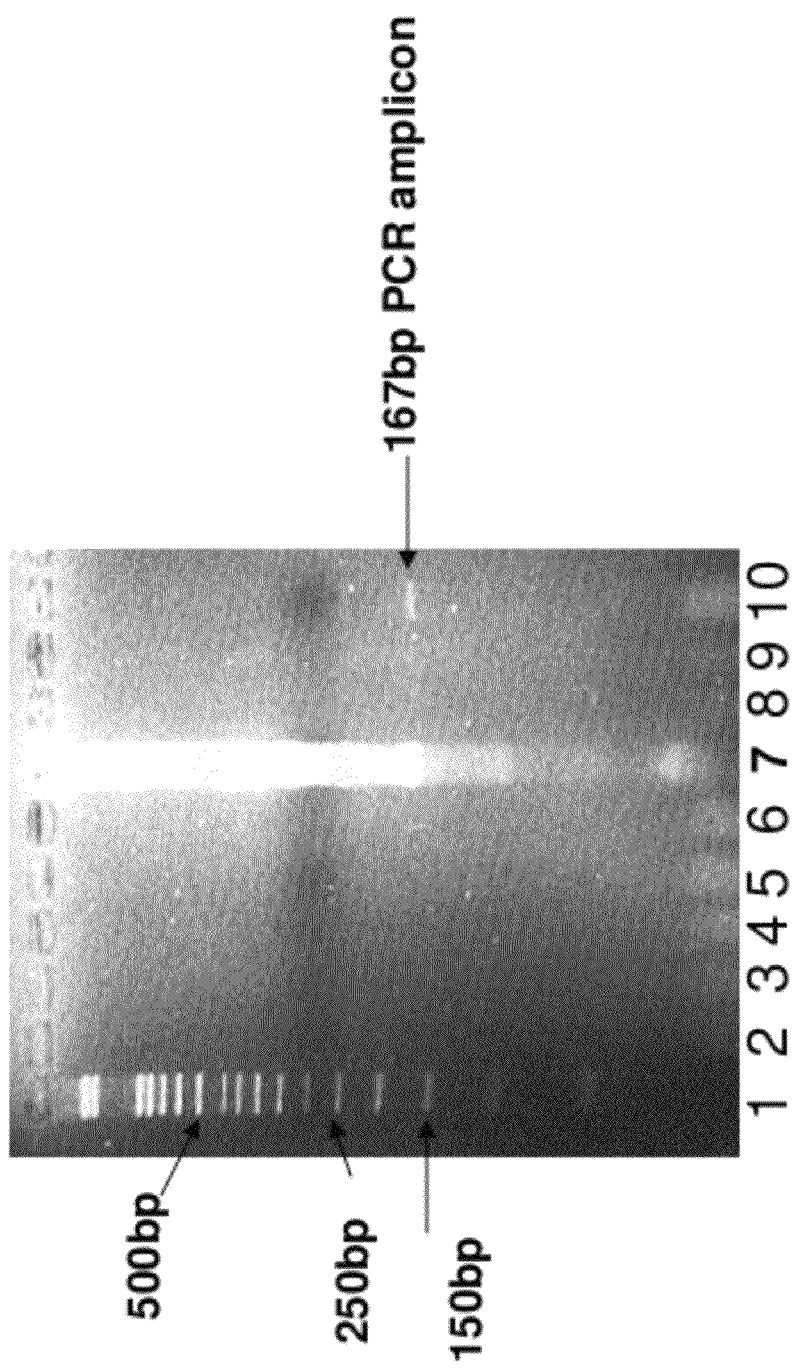
FIG. 8 is an electrophoretic analysis of PCR products generated from the sample recovered in Example 19 after elution of DNA from the magnetic microparticle-nanoparticle-DNA triplex.

FIG. 8 is an electrophoretic analysis of PCR products generated from the samples recovered after elution of DNA from the magnetic microparticle-nanoparticle-DNA triplex. Lane 1 contains a 50 bp DNA Ladder. Lane 7 contains of the PCR product from 200 ng of purified genomic DNA as a positive control. Lane 8 is the negative control of the PCR assay with no template DNA. Lanes 9 and 10 contain PCR products generated from the samples recovered after elution of DNA from the magnetic microparticle-nanoparticle-DNA triplex. The PCR product in lane 9 was generated from 1 μL of the eluted sample used as the template, and the PCR product in lane 10 was generated from 2 μL of the eluted sample used as the template. The PCR reactions contained primers for six DNA targets in a rigorous, multiplex DNA PCR reaction with the targets measuring 551, 473, 398, 330, 249 and 167 base pairs. Amplification of the 167 bp amplicon from an isoform of the glutathione s-transferase gene is seen in Lane 10, indicating that DNA was successfully eluted from the nanoparticle-magnetic microparticle complex. The absorbance spectrum for the DNA used for the PCR reaction shown in lane 10 of FIG. 8 is shown in FIG. 7B. This Example demonstrates the binding of DNA to the nanoparticles, the self-assembly of the nanoparticles onto the magnetic beads, and the recovery of DNA from these complexes.

Example 20

Self Assembly of DNA-Magnetic Nanoparticle Complexes

The general procedure followed for the magnetic nanoparticle technology is as follows. Magnetic nanoparticles are added to a dilute DNA solution. The magnetic nanoparticles may be treated to isolate a variety of biomolecules. The DNA is allowed to bind to the magnetic nanoparticles. The DNA is then harvested as a DNA-magnetic nanoparticle complex by forming a pellet of the magnetic nanoparticles, using a magnetic field. The pellet is then washed to remove contaminants. The DNA is then eluted from the magnetic nanoparticles and recovered.

All references cited in this application are incorporated by reference herein in their entireties. While the present invention has been described with reference to its preferred embodiments and the foregoing non-limiting examples, those skilled in the art will understand and appreciate that the scope of the present invention is intended to be limited only the claims appended hereto.

The invention claimed is:

1. A method of separating biomolecules from a sample, comprising the steps of:
   a) providing a solid phase nanoparticle matrix comprising nanoparticles having a surface area to volume ratio (m2/cm3) greater than 10, and densities (p) of 2 or more;
   b) selecting a subset of the nanoparticles having sedimentation rates in water where the sedimentation velocity is between about 0.1 cm/min at 10,000 G (Vmin) and about 2 cm/min at 500 G (Vmax) at standard temperature and pressure, and wherein the subset of nanoparticles form a colloidal suspension in aqueous solution;
   c) treating the sample with the subset of nanoparticles forming the solid phase nanoparticle matrix in colloidal suspension and allowing biomolecules from the sample to bind to the subset of nanoparticles forming the solid phase nanoparticle matrix, thereby forming biomolecule-nanoparticle complexes;
   d) adding magnetic beads to the sample and allowing the biomolecule-nanoparticle complexes to associate with the magnetic beads, thereby forming biomolecule-nanoparticle-magnetic bead complexes;
   e) partitioning the biomolecule-nanoparticle-magnetic bead complexes from the colloidal suspension by exposing the sample to a magnetic field;
   f) eluting the bound biomolecules from the biomolecule-nanoparticle-magnetic bead complexes; and
   g) recovering the eluted biomolecules.

2. The method of claim 1, wherein the solid-phase nanoparticle matrix further comprises particles having a molecular coating specific for binding a predetermined class of biomolecule.

3. The method of claim 2, wherein the biomolecule is selected from the group consisting of DNA, RNA, immunoglobulin, protein, and peptide.

4. The method of claim 1, wherein the solid-phase nanoparticle matrix further comprises particles selected from the group consisting of (a) metals, semi-metals, and non-metals and their corresponding oxides, carbides, hydroxides, nitrides, phosphates, alloys, and silicates, (b) ceramics, clays, glasses, crystals and mixtures thereof, and (c) linear or branched polymers comprised of carbon, germanium, silicon, or complexes thereof.

5. The method of claim 4, wherein the solid-phase nanoparticle matrix further comprises a clay selected from the group consisting of naturally derived mineral mixtures silicates, metal silicates, phyllo silicates, kaolinates, kaolin, micas, smectites, montmollinites, bentonite, quartzes, aluminosilicates, and magnesium silicates, and talc, in the form of crystals, ceramics, or glasses.

6. The method of claim 4, wherein the solid-phase nanoparticle matrix further comprises an oxide of a metal, semi-metal, or non-metal.

7. The method of claim 6, wherein the oxide is selected from the group consisting of tin oxide, titanium oxide, zirconium oxide, aluminum oxide, and tungsten oxide.

8. The method of claim 2, wherein the molecular coating is selected from the group consisting of alkanes, amines, carboxylates, detergents, neutral polymers, oxyanions, organosilanes, and mixtures thereof.

9. The method of claim 8, wherein the solid phase nanoparticle matrix is treated with borate, and the magnetic beads are coated with polymers of polyalcohols or polysaccharides.

10. The method of claim 8, wherein the solid phase nanoparticle matrix is treated with phosphate, and the magnetic beads are coated with a polycarboxylate.

11. The method of claim 8, wherein the solid phase nanoparticle matrix and the magnetic beads are coated with borate.

12. The method of claim 8, wherein the solid phase nanoparticle matrix and the magnetic beads are coated with a thiophilic structure.

13. A method of separating biomolecules from a sample, comprising the steps of:
   a) providing a solid phase, magnetic nanoparticle matrix comprising nanoparticles having a surface area to volume ratio (m2/cm3) greater than 10, and densities (p) of 2 or more;
   b) selecting a subset of the nanoparticles having sedimentation rates in water where the sedimentation velocity is between about 0.1 cm/min at 10,000 G (Vmin) and about 2 cm/min at 500 G (Vmax) at standard temperature and pressure, and wherein the subset of nanoparticles form a colloidal suspension in aqueous solution;
   c) treating the sample with the subset of nanoparticles forming the solid phase, magnetic nanoparticle matrix in colloidal suspension and allowing biomolecules from the sample to bind to the subset of nanoparticles forming the solid phase, magnetic nanoparticle matrix in colloidal suspension, thereby forming biomolecule-magnetic nanoparticle complexes;
   d) partitioning the biomolecule-magnetic nanoparticle complexes from the colloidal suspension by exposing the treated sample to a magnetic field;
   e) eluting the bound biomolecules from the biomolecule-magnetic nanoparticle complexes; and
   f) recovering the eluted biomolecules.

14. The method of claim 13 wherein the solid phase, magnetic nanoparticle matrix comprises a non-ferrous magnetic material.

15. The method of claim 13 wherein the solid phase, magnetic nanoparticle matrix further comprises particles having a molecular coating specific for binding a predetermined class of biomolecule.

16. The method of claim 15, wherein the biomolecule is selected from the group consisting of DNA, RNA, immunoglobulin, protein, and peptide.

* * * * *